US010221430B2

United States Patent
Thayer et al.

(10) Patent No.: US 10,221,430 B2
(45) Date of Patent: Mar. 5, 2019

(54) AXMI440 TOXIN GENE AND METHODS FOR ITS USE

(71) Applicant: Athenix Corp., Morrisville, NC (US)

(72) Inventors: Rebecca Thayer, Morrisville, NC (US); Kimberly S. Sampson, Durham, NC (US); Duane Lehtinen, Cary, NC (US); Leonardo Magalhaes, Durham, NC (US)

(73) Assignee: BASF SE, Ludwigshafen am Rhein (DE)

( * ) Notice: Subject to any disclaimer, the term of this patent is extended or adjusted under 35 U.S.C. 154(b) by 128 days.

(21) Appl. No.: 14/910,474

(22) PCT Filed: Aug. 8, 2014

(86) PCT No.: PCT/US2014/050327
§ 371 (c)(1),
(2) Date: Feb. 5, 2016

(87) PCT Pub. No.: WO2015/041769
PCT Pub. Date: Mar. 26, 2015

(65) Prior Publication Data
US 2016/0185830 A1 Jun. 30, 2016

Related U.S. Application Data

(60) Provisional application No. 61/863,982, filed on Aug. 9, 2013.

(51) Int. Cl.
*C12N 15/82* (2006.01)
*C07K 14/325* (2006.01)

(52) U.S. Cl.
CPC ........ *C12N 15/8286* (2013.01); *C07K 14/325* (2013.01)

(58) Field of Classification Search
None
See application file for complete search history.

(56) References Cited

FOREIGN PATENT DOCUMENTS

WO 2007147096 A2 12/2007
WO 2011014749 A1 2/2011

OTHER PUBLICATIONS

Argôlo-Filho & Loguercio, Insects 5:62-91 (2014).*
Ye, W., et al., Mining New Crystal Protein Genes from Bacillus Thuringiensis on the Basis of Mixed Plasmid-Enriched Genome Sequencing and a Computational Pipeline, Applied and Environmental Microbiology, Jul. 15, 2012, pp. 4795-4801, vol. 78, No. 14.
Sheppard, A.E., et al., Complete Genome Sequence of Bacillus Thuringiensis Strain 407 Cry, Genome Announcements, Feb. 28, 2013, po. e00158-12, vol. 1, No. 1.
Naranjo, Steven E., Impacts of Bt Transgenic Cotton on Integrated Pest Management, Journal of Agricultural and Food Chemistry, Jun. 8, 2011, pp. 5842-5851, vol. 59, No. 11.
Pardo-Lopez, Liliana, et al., Bacillus Thuringiensis Insecticidal three-domain Cry toxins: Mode of Action, Insect Resistance and Consequences for Crop Protection, FEMS Microbiology Reviews, Jan. 11, 2013, pp. 3-22, vol. 37, No. 1.
International Search Report for International Application No. PCT/US2014/050327 dated Mar. 23, 2015, pp. 1-10.

* cited by examiner

*Primary Examiner* — Russell T Boggs

(57) ABSTRACT

Compositions and methods for conferring pesticidal activity to bacteria, plants, plant cells, tissues and seeds are provided. Compositions comprising a coding sequence for a toxin polypeptide are provided. The coding sequences can be used in DNA constructs or expression cassettes for transformation and expression in plants and bacteria. Compositions also comprise transformed bacteria, plants, plant cells, tissues, and seeds. In particular, isolated toxin nucleic acid molecules are provided. Additionally, amino acid sequences corresponding to the polynucleotides are encompassed, and antibodies specifically binding to those amino acid sequences. In particular, the present invention provides for isolated nucleic acid molecules comprising nucleotide sequences encoding the amino acid sequence shown in SEQ ID NO:3-6, or the nucleotide sequence set forth in SEQ ID NO: 1 or 2, as well as variants and fragments thereof.

18 Claims, No Drawings

Specification includes a Sequence Listing.

AXMI440 TOXIN GENE AND METHODS FOR ITS USE

FIELD OF THE INVENTION

This invention relates to the field of molecular biology. Provided are novel genes that encode pesticidal proteins. These proteins and the nucleic acid sequences that encode them are useful in preparing pesticidal formulations and in the production of transgenic pest-resistant plants.

BACKGROUND OF THE INVENTION

*Bacillus thuringiensis* is a Gram-positive spore forming soil bacterium characterized by its ability to produce crystalline inclusions that are specifically toxic to certain orders and species of insects, but are harmless to plants and other non-targeted organisms. For this reason, compositions including *Bacillus thuringiensis* strains or their insecticidal proteins can be used as environmentally-acceptable insecticides to control agricultural insect pests or insect vectors for a variety of human or animal diseases.

Crystal (Cry) proteins (delta-endotoxins) from *Bacillus thuringiensis* have potent insecticidal activity against predominantly Lepidopteran, Hemipteran, Dipteran, and Coleopteran larvae. These proteins also have shown activity against Hymenoptera, Homoptera, Phthiraptera, Mallophaga, and Acari pest orders, as well as other invertebrate orders such as Nemathelminthes, Platyhelminthes, and Sarcomastigorphora (Feitelson (1993) The *Bacillus Thuringiensis* family tree. In *Advanced Engineered Pesticides*, Marcel Dekker, Inc., New York, N.Y.) These proteins were originally classified as CryI to CryV based primarily on their insecticidal activity. The major classes were Lepidoptera-specific (I), Lepidoptera- and Diptera-specific (II), Coleoptera-specific (III), Diptera-specific (IV), and nematode-specific (V) and (VI). The proteins were further classified into subfamilies; more highly related proteins within each family were assigned divisional letters such as Cry1A, Cry1B, Cry1C, etc. Even more closely related proteins within each division were given names such as Cry1C1, Cry1C2, etc.

A nomenclature was described for the Cry genes based upon amino acid sequence homology rather than insect target specificity (Crickmore et al. (1998) *Microbiol. Mol. Biol. Rev.* 62:807-813). In this classification, each toxin is assigned a unique name incorporating a primary rank (an Arabic number), a secondary rank (an uppercase letter), a tertiary rank (a lowercase letter), and a quaternary rank (another Arabic number). Roman numerals have been exchanged for Arabic numerals in the primary rank. Proteins with less than 45% sequence identity have different primary ranks, and the criteria for secondary and tertiary ranks are 78% and 95%, respectively.

The crystal protein does not exhibit insecticidal activity until it has been ingested and solubilized in the insect midgut. The ingested protoxin is hydrolyzed by proteases in the insect digestive tract to an active toxic molecule. (Höfte and Whiteley (1989) *Microbiol. Rev.* 53:242-255). This toxin binds to apical brush border receptors in the midgut of the target larvae and inserts into the apical membrane creating ion channels or pores, resulting in larval death.

Delta-endotoxins generally have five conserved sequence domains, and three conserved structural domains (see, for example, de Maagd et al. (2001) *Trends Genetics* 17:193-199). The first conserved structural domain consists of seven alpha helices and is involved in membrane insertion and pore formation. Domain II consists of three beta-sheets arranged in a Greek key configuration, and domain III consists of two antiparallel beta-sheets in "jelly-roll" formation (de Maagd et al., 2001, supra). Domains II and III are involved in receptor recognition and binding, and are therefore considered determinants of toxin specificity.

Because of the devastation that insects can confer, and the improvement in yield by controlling insect pests, there is a continual need to discover new forms of pesticidal toxins.

SUMMARY OF INVENTION

Compositions and methods for conferring pesticidal activity to bacteria, plants, plant cells, tissues and seeds are provided. Compositions include nucleic acid molecules encoding sequences for pesticidal and insectidal polypeptides, vectors comprising those nucleic acid molecules, and host cells comprising the vectors. Compositions also include the pesticidal polypeptide sequences and antibodies to those polypeptides. The nucleotide sequences can be used in DNA constructs or expression cassettes for transformation and expression in organisms, including microorganisms and plants. The nucleotide or amino acid sequences may be synthetic sequences that have been designed for expression in an organism including, but not limited to, a microorganism or a plant. Compositions also comprise bacteria, plants, plant cells, tissues, and seeds comprising the nucleotide sequence of the invention.

In particular, isolated or recombinant nucleic acid molecules are provided that encode a pesticidal protein. Additionally, amino acid sequences corresponding to the pesticidal protein are encompassed. In particular, the present invention provides for an isolated or recombinant nucleic acid molecule comprising a nucleotide sequence encoding the amino acid sequence shown in SEQ ID NO:3-6 or a nucleotide sequence set forth in SEQ ID NO:1 or 2, as well as biologically-active variants and fragments thereof. Nucleotide sequences that are complementary to a nucleotide sequence of the invention, or that hybridize to a sequence of the invention or a complement thereof are also encompassed. Further provided are vectors, host cells, plants, and seeds comprising the nucleotide sequences of the invention, or nucleotide sequences encoding the amino acid sequences of the invention, as well as biologically-active variants and fragments thereof.

Methods are provided for producing the polypeptides of the invention, and for using those polypeptides for controlling or killing a lepidopteran, hemipteran, coleopteran, nematode, or dipteran pest. Methods and kits for detecting the nucleic acids and polypeptides of the invention in a sample are also included.

The compositions and methods of the invention are useful for the production of organisms with enhanced pest resistance or tolerance. These organisms and compositions comprising the organisms are desirable for agricultural purposes. The compositions of the invention are also useful for generating altered or improved proteins that have pesticidal activity, or for detecting the presence of pesticidal proteins or nucleic acids in products or organisms.

DETAILED DESCRIPTION

The present invention is drawn to compositions and methods for regulating pest resistance or tolerance in organisms, particularly plants or plant cells. By "resistance" is intended that the pest (e.g., insect) is killed upon ingestion or other contact with the polypeptides of the invention. By "tolerance" is intended an impairment or reduction in the movement, feeding, reproduction, or other functions of the pest. The methods involve transforming organisms with a nucleotide sequence encoding a pesticidal protein of the invention. In particular, the nucleotide sequences of the invention are useful for preparing plants and microorganisms that possess pesticidal activity. Thus, transformed bacteria, plants, plant cells, plant tissues and seeds are provided. Compositions are pesticidal nucleic acids and proteins of *Bacillus* or other species. The sequences find use in the construction of expression vectors for subsequent transformation into organisms of interest, as probes for the isolation of other homologous (or partially homologous) genes, and for the generation of altered pesticidal proteins by methods known in the art, such as domain swapping or DNA shuffling, for example, with members of the Cry1, Cry2, and Cry9 families of endotoxins. The proteins find use in controlling or killing lepidopteran, hemipteran, coleopteran, dipteran, and nematode pest populations and for producing compositions with pesticidal activity.

By "pesticidal toxin" or "pesticidal protein" is intended a toxin that has toxic activity against one or more pests, including, but not limited to, members of the Lepidoptera, Diptera, Hemiptera and Coleoptera orders, or the Nematoda phylum, or a protein that has homology to such a protein. Pesticidal proteins have been isolated from organisms including, for example, *Bacillus* sp., *Clostridium bifermentans* and *Paenibacillus popilliae*. Pesticidal proteins include amino acid sequences deduced from the full-length nucleotide sequences disclosed herein, and amino acid sequences that are shorter than the full-length sequences, either due to the use of an alternate downstream start site, or due to processing that produces a shorter protein having pesticidal activity. Processing may occur in the organism the protein is expressed in, or in the pest after ingestion of the protein.

Thus, provided herein are novel isolated or recombinant nucleotide sequences that confer pesticidal activity. These nucleotide sequences encode polypeptides with homology to known delta-endotoxins or binary toxins. Also provided are the amino acid sequences of the pesticidal proteins. The protein resulting from translation of this gene allows cells to control or kill pests that ingest it.

Isolated Nucleic Acid Molecules, and Variants and Fragments Thereof

One aspect of the invention pertains to isolated or recombinant nucleic acid molecules comprising nucleotide sequences encoding pesticidal proteins and polypeptides or biologically active portions thereof, as well as nucleic acid molecules sufficient for use as hybridization probes to identify nucleic acid molecules encoding proteins with regions of sequence homology. Also encompassed herein are nucleotide sequences capable of hybridizing to the nucleotide sequences of the invention under stringent conditions as defined elsewhere herein. As used herein, the term "nucleic acid molecule" is intended to include DNA molecules (e.g., recombinant DNA, cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

An "isolated" or "recombinant" nucleic acid sequence (or DNA) is used herein to refer to a nucleic acid sequence (or DNA) that is no longer in its natural environment, for example in an in vitro or in a recombinant bacterial or plant host cell. In some embodiments, an isolated or recombinant nucleic acid is free of sequences (preferably protein encoding sequences) that naturally flank the nucleic acid (i.e., sequences located at the 5' and 3' ends of the nucleic acid) in the genomic DNA of the organism from which the nucleic acid is derived. For purposes of the invention, "isolated" when used to refer to nucleic acid molecules excludes isolated chromosomes. For example, in various embodiments, the isolated delta-endotoxin encoding nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived. In various embodiments, a delta-endotoxin protein that is substantially free of cellular material includes preparations of protein having less than about 30%, 20%, 10%, or 5% (by dry weight) of non-delta-endotoxin protein (also referred to herein as a "contaminating protein"). In some embodiments, the recombinant nucleic acid of the invention comprises one or more nucleotide substitutions relative to SEQ ID NO:1, or a variant or fragment thereof.

Nucleotide sequences encoding the proteins of the present invention include the sequence set forth in SEQ ID NO:1 or 2, and variants, fragments, and complements thereof. By "complement" is intended a nucleotide sequence that is sufficiently complementary to a given nucleotide sequence such that it can hybridize to the given nucleotide sequence to thereby form a stable duplex. The corresponding amino acid sequences for the pesticidal proteins encoded by these nucleotide sequences are set forth in SEQ ID NO:3-6.

Nucleic acid molecules that are fragments of these nucleotide sequences encoding pesticidal proteins are also encompassed by the present invention. By "fragment" is intended a portion of the nucleotide sequence encoding a pesticidal protein. A fragment of a nucleotide sequence may encode a biologically active portion of a pesticidal protein, or it may be a fragment that can be used as a hybridization probe or PCR primer using methods disclosed below. Nucleic acid molecules that are fragments of a nucleotide sequence encoding a pesticidal protein comprise at least about 50, 100, 200, 300, 400, 500, 600, 700, 800, 900, 1000, 1100, 1200, 1300, 1350, 1400 contiguous nucleotides, or up to the number of nucleotides present in a full-length nucleotide sequence encoding a pesticidal protein disclosed herein, depending upon the intended use. By "contiguous" nucleotides is intended nucleotide residues that are immediately adjacent to one another. Fragments of the nucleotide sequences of the present invention will encode protein fragments that retain the biological activity of the pesticidal protein and, hence, retain pesticidal activity. Thus, biologically-active fragments of the polypeptides disclosed herein are also encompassed. By "retains activity" is intended that the fragment will have at least about 30%, at least about 50%, at least about 70%, 80%, 90%, 95% or higher of the pesticidal activity of the pesticidal protein. In one embodiment, the pesticidal activity is coleoptericidal activity. In another embodiment, the pesticidal activity is lepidoptericidal activity. In another embodiment, the pesticidal activity is nematocidal activity. In another embodiment, the pesticidal activity is diptericidal activity. In another embodiment, the pesticidal activity is hemiptericidal activity. Methods for measuring pesticidal activity are well known in the art. See, for example, Czapla and Lang (1990) *J. Econ. Entomol.* 83:2480-2485; Andrews et al. (1988) *Biochem. J.* 252:199-206; Marrone et al. (1985) *J. of Economic Entomology* 78:290-293; and U.S. Pat. No. 5,743,477, all of which are herein incorporated by reference in their entirety.

A fragment of a nucleotide sequence encoding a pesticidal protein that encodes a biologically active portion of a protein of the invention will encode at least about 15, 25, 30, 50, 75, 100, 125, 150, 175, 200, 250, 300, 350, 400, 450 contiguous amino acids, or up to the total number of amino acids present in a full-length pesticidal protein of the invention. In some embodiments, the fragment is a proteolytic cleavage fragment. For example, the proteolytic cleavage fragment may have an N-terminal or a C-terminal truncation of at least about 100 amino acids, about 120, about 130, about 140, about 150, or about 160 amino acids relative to SEQ ID NO:3-6. In some embodiments, the fragments encompassed herein result from the removal of the C-terminal crystallization domain, e.g., by proteolysis or by insertion of a stop codon in the coding sequence.

Preferred pesticidal proteins of the present invention are encoded by a nucleotide sequence sufficiently identical to the nucleotide sequence of SEQ ID NO:1 or 2, or the pesticidal proteins are sufficiently identical to the amino acid sequence set forth in SEQ ID NO:3-6. By "sufficiently identical" is intended an amino acid or nucleotide sequence that has at least about 60% or 65% sequence identity, about 70% or 75% sequence identity, about 80% or 85% sequence identity, about 90%, 91%, 92%, 93%, 94%, 95%, 96%, 97%, 98%, 99% or greater sequence identity compared to a reference sequence using one of the alignment programs described herein using standard parameters. One of skill in the art will recognize that these values can be appropriately adjusted to determine corresponding identity of proteins encoded by two nucleotide sequences by taking into account codon degeneracy, amino acid similarity, reading frame positioning, and the like.

To determine the percent identity of two amino acid sequences or of two nucleic acids, the sequences are aligned for optimal comparison purposes. The percent identity between the two sequences is a function of the number of identical positions shared by the sequences (i.e., percent identity=number of identical positions/total number of positions (e.g., overlapping positions)×100). In one embodiment, the two sequences are the same length. In another embodiment, the percent identity is calculated across the entirety of the reference sequence (i.e., the sequence disclosed herein as any of SEQ ID NO:1-6). The percent identity between two sequences can be determined using techniques similar to those described below, with or without allowing gaps. In calculating percent identity, typically exact matches are counted. A gap, i.e. a position in an alignment where a residue is present in one sequence but not in the other, is regarded as a position with non-identical residues.

The determination of percent identity between two sequences can be accomplished using a mathematical algorithm. A nonlimiting example of a mathematical algorithm utilized for the comparison of two sequences is the algorithm of Karlin and Altschul (1990) *Proc. Natl. Acad. Sci. USA* 87:2264, modified as in Karlin and Altschul (1993) *Proc. Natl. Acad. Sci. USA* 90:5873-5877. Such an algorithm is incorporated into the BLASTN and BLASTX programs of Altschul et al. (1990) *J. Mol. Biol.* 215:403. BLAST nucleotide searches can be performed with the BLASTN program, score=100, wordlength=12, to obtain nucleotide sequences homologous to pesticidal-like nucleic acid molecules of the invention. BLAST protein searches can be performed with the BLASTX program, score=50, wordlength=3, to obtain amino acid sequences homologous to pesticidal protein molecules of the invention. To obtain gapped alignments for comparison purposes, Gapped BLAST (in BLAST 2.0) can be utilized as described in Altschul et al. (1997) *Nucleic Acids Res.* 25:3389. Alternatively, PSI-Blast can be used to perform an iterated search that detects distant relationships between molecules. See Altschul et al. (1997) supra. When utilizing BLAST, Gapped BLAST, and PSI-Blast programs, the default parameters of the respective programs (e.g., BLASTX and BLASTN) can be used. Alignment may also be performed manually by inspection.

Another non-limiting example of a mathematical algorithm utilized for the comparison of sequences is the ClustalW algorithm (Higgins et al. (1994) *Nucleic Acids Res.* 22:4673-4680). ClustalW compares sequences and aligns the entirety of the amino acid or DNA sequence, and thus can provide data about the sequence conservation of the entire amino acid sequence. The ClustalW algorithm is used in several commercially available DNA/amino acid analysis software packages, such as the ALIGNX module of the Vector NTI Program Suite (Invitrogen Corporation, Carlsbad, Calif.). After alignment of amino acid sequences with ClustalW, the percent amino acid identity can be assessed. A non-limiting example of a software program useful for analysis of ClustalW alignments is GENEDOC™. GENEDOC™ (Karl Nicholas) allows assessment of amino acid (or DNA) similarity and identity between multiple proteins. Another non-limiting example of a mathematical algorithm utilized for the comparison of sequences is the algorithm of Myers and Miller (1988) *CABIOS* 4:11-17. Such an algorithm is incorporated into the ALIGN program (version 2.0), which is part of the GCG Wisconsin Genetics Software Package, Version 10 (available from Accelrys, Inc., 9685 Scranton Rd., San Diego, Calif., USA). When utilizing the ALIGN program for comparing amino acid sequences, a PAM120 weight residue table, a gap length penalty of 12, and a gap penalty of 4 can be used.

Unless otherwise stated, GAP Version 10, which uses the algorithm of Needleman and Wunsch (1970) *J. Mol. Biol.* 48(3):443-453, will be used to determine sequence identity or similarity using the following parameters: % identity and % similarity for a nucleotide sequence using GAP Weight of 50 and Length Weight of 3, and the nwsgapdna.cmp scoring matrix; % identity or % similarity for an amino acid sequence using GAP weight of 8 and length weight of 2, and the BLOSUM62 scoring program. Equivalent programs may also be used. By "equivalent program" is intended any sequence comparison program that, for any two sequences in question, generates an alignment having identical nucleotide residue matches and an identical percent sequence identity when compared to the corresponding alignment generated by GAP Version 10.

The invention also encompasses variant nucleic acid molecules. "Variants" of the pesticidal protein encoding nucleotide sequences include those sequences that encode the pesticidal proteins disclosed herein but that differ conservatively because of the degeneracy of the genetic code as well as those that are sufficiently identical as discussed above. Naturally occurring allelic variants can be identified with the use of well-known molecular biology techniques, such as polymerase chain reaction (PCR) and hybridization techniques as outlined below. Variant nucleotide sequences also include synthetically derived nucleotide sequences that have been generated, for example, by using site-directed mutagenesis but which still encode the pesticidal proteins disclosed in the present invention as discussed below. Variant proteins encompassed by the present invention are biologically active, that is they continue to possess the desired biological activity of the native protein, that is, pesticidal activity. By "retains activity" is intended that the variant will have at least about 30%, at least about 50%, at least about 70%, or at least about 80% of the pesticidal activity of the native protein. Methods for measuring pesticidal activity are well known in the art. See, for example, Czapla and Lang (1990) *J. Econ. Entomol.* 83: 2480-2485;

Andrews et al. (1988) *Biochem. J.* 252:199-206; Marrone et al. (1985) *J. of Economic Entomology* 78:290-293; and U.S. Pat. No. 5,743,477, all of which are herein incorporated by reference in their entirety.

The skilled artisan will further appreciate that changes can be introduced by mutation of the nucleotide sequences of the invention thereby leading to changes in the amino acid sequence of the encoded pesticidal proteins, without altering the biological activity of the proteins. Thus, variant isolated nucleic acid molecules can be created by introducing one or more nucleotide substitutions, additions, or deletions into the corresponding nucleotide sequence disclosed herein, such that one or more amino acid substitutions, additions or deletions are introduced into the encoded protein. Mutations can be introduced by standard techniques, such as site-directed mutagenesis and PCR-mediated mutagenesis. Such variant nucleotide sequences are also encompassed by the present invention.

For example, conservative amino acid substitutions may be made at one or more, predicted, nonessential amino acid residues. A "nonessential" amino acid residue is a residue that can be altered from the wild-type sequence of a pesticidal protein without altering the biological activity, whereas an "essential" amino acid residue is required for biological activity. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

Delta-endotoxins generally have five conserved sequence domains, and three conserved structural domains (see, for example, de Maagd et al. (2001) Trends Genetics 17:193-199). The first conserved structural domain consists of seven alpha helices and is involved in membrane insertion and pore formation. Domain II consists of three beta-sheets arranged in a Greek key configuration, and domain III consists of two antiparallel beta-sheets in "jelly-roll" formation (de Maagd et al., 2001, supra). Domains II and III are involved in receptor recognition and binding, and are therefore considered determinants of toxin specificity.

Amino acid substitutions may be made in nonconserved regions that retain function. In general, such substitutions would not be made for conserved amino acid residues, or for amino acid residues residing within a conserved motif, where such residues are essential for protein activity. Examples of residues that are conserved and that may be essential for protein activity include, for example, residues that are identical between all proteins contained in an alignment of similar or related toxins to the sequences of the invention (e.g., residues that are identical in an alignment of homologous proteins). Examples of residues that are conserved but that may allow conservative amino acid substitutions and still retain activity include, for example, residues that have only conservative substitutions between all proteins contained in an alignment of similar or related toxins to the sequences of the invention (e.g., residues that have only conservative substitutions between all proteins contained in the alignment homologous proteins). However, one of skill in the art would understand that functional variants may have minor conserved or nonconserved alterations in the conserved residues.

Alternatively, variant nucleotide sequences can be made by introducing mutations randomly along all or part of the coding sequence, such as by saturation mutagenesis, and the resultant mutants can be screened for ability to confer pesticidal activity to identify mutants that retain activity. Following mutagenesis, the encoded protein can be expressed recombinantly, and the activity of the protein can be determined using standard assay techniques.

Using methods such as PCR, hybridization, and the like corresponding pesticidal sequences can be identified, such sequences having substantial identity to the sequences of the invention. See, for example, Sambrook and Russell (2001) *Molecular Cloning: A Laboratory Manual*. (Cold Spring Harbor Laboratory Press, Cold Spring Harbor, N.Y.) and Innis, et al. (1990) *PCR Protocols: A Guide to Methods and Applications* (Academic Press, N.Y.).

In a hybridization method, all or part of the pesticidal nucleotide sequence can be used to screen cDNA or genomic libraries. Methods for construction of such cDNA and genomic libraries are generally known in the art and are disclosed in Sambrook and Russell, 2001, supra. The so-called hybridization probes may be genomic DNA fragments, cDNA fragments, RNA fragments, or other oligonucleotides, and may be labeled with a detectable group such as $^{32}P$, or any other detectable marker, such as other radioisotopes, a fluorescent compound, an enzyme, or an enzyme co-factor. Probes for hybridization can be made by labeling synthetic oligonucleotides based on the known pesticidal protein-encoding nucleotide sequence disclosed herein. Degenerate primers designed on the basis of conserved nucleotides or amino acid residues in the nucleotide sequence or encoded amino acid sequence can additionally be used. The probe typically comprises a region of nucleotide sequence that hybridizes under stringent conditions to at least about 12, at least about 25, at least about 50, 75, 100, 125, 150, 175, or 200 consecutive nucleotides of nucleotide sequence encoding a pesticidal protein of the invention or a fragment or variant thereof. Methods for the preparation of probes for hybridization are generally known in the art and are disclosed in Sambrook and Russell, 2001, supra herein incorporated by reference.

For example, an entire pesticidal sequence disclosed herein, or one or more portions thereof, may be used as a probe capable of specifically hybridizing to corresponding pesticidal protein-like sequences and messenger RNAs. To achieve specific hybridization under a variety of conditions, such probes include sequences that are unique and are preferably at least about 10 nucleotides in length, or at least about 20 nucleotides in length. Such probes may be used to amplify corresponding pesticidal sequences from a chosen organism by PCR. This technique may be used to isolate additional coding sequences from a desired organism or as a diagnostic assay to determine the presence of coding sequences in an organism. Hybridization techniques include hybridization screening of plated DNA libraries (either plaques or colonies; see, for example, Sambrook et al. (1989) *Molecular Cloning: A Laboratory Manual* (2d ed., Cold Spring Harbor Laboratory Press, Cold Spring Harbor, N.Y.).

Thus, the present invention encompasses probes for hybridization, as well as nucleotide sequences capable of hybridization to all or a portion of a nucleotide sequence of the invention (e.g., at least about 300 nucleotides, at least about 400, at least about 500, 1000, 1200, 1500, 2000, 2500, 3000, 3500, or up to the full length of a nucleotide sequence disclosed herein). Hybridization of such sequences may be carried out under stringent conditions. By "stringent conditions" or "stringent hybridization conditions" is intended conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, preferably less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. Optionally, wash buffers may comprise about 0.1% to about 1% SDS. Duration of hybridization is generally less than about 24 hours, usually about 4 to about 12 hours.

Specificity is typically the function of post-hybridization washes, the critical factors being the ionic strength and temperature of the final wash solution. For DNA-DNA hybrids, the $T_m$ can be approximated from the equation of Meinkoth and Wahl (1984) *Anal. Biochem.* 138:267-284: $T_m$=81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted to hybridize to sequences of the desired identity. For example, if sequences with ≥90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is preferred to increase the SSC concentration so that a higher temperature can be used. An extensive guide to the hybridization of nucleic acids is found in Tijssen (1993) *Laboratory Techniques in Biochemistry and Molecular Biology—Hybridization with Nucleic Acid Probes*, Part I, Chapter 2 (Elsevier, N.Y.); and Ausubel et al., eds. (1995) *Current Protocols in Molecular Biology*, Chapter 2 (Greene Publishing and Wiley-Interscience, New York). See Sambrook et al. (1989) *Molecular Cloning: A Laboratory Manual* (2d ed., Cold Spring Harbor Laboratory Press, Cold Spring Harbor, N.Y.).

Isolated Proteins and Variants and Fragments Thereof

Pesticidal proteins are also encompassed within the present invention. By "pesticidal protein" is intended a protein having the amino acid sequence set forth in SEQ ID NO:3-6. Fragments, biologically active portions, and variants thereof are also provided, and may be used to practice the methods of the present invention. An "isolated protein" or a "recombinant protein" is used to refer to a protein that is no longer in its natural environment, for example in vitro or in a recombinant bacterial or plant host cell. In some embodiments, the recombinant protein is a variant of SEQ ID NO:2-5, wherein the variant comprises at least one amino acid substitution, deletion, or insertion relative to SEQ ID NO:2-5.

"Fragments" or "biologically active portions" include polypeptide fragments comprising amino acid sequences sufficiently identical to the amino acid sequence set forth in SEQ ID NO:3-6, and that exhibit pesticidal activity. A biologically active portion of a pesticidal protein can be a polypeptide that is, for example, 10, 25, 50, 100, 150, 200, 250, 300, 350, 400, 450, 500, 550, 600, 650, 700, 750, 800, 850, 900, 950, 1000, 1050, 1100, 1150, 1200, 1250, 1300, 1350, or more amino acids in length. Such biologically active portions can be prepared by recombinant techniques and evaluated for pesticidal activity. Methods for measuring pesticidal activity are well known in the art. See, for example, Czapla and Lang (1990) *J. Econ. Entomol.* 83:2480-2485; Andrews et al. (1988) *Biochem. J.* 252:199-206; Marrone et al. (1985) *J. of Economic Entomology* 78:290-293; and U.S. Pat. No. 5,743,477, all of which are herein incorporated by reference in their entirety. As used here, a fragment comprises at least 8 contiguous amino acids of SEQ ID NO:3-6. The invention encompasses other fragments, however, such as any fragment in the protein greater than about 10, 20, 30, 50, 100, 150, 200, 250, 300, 350, 400, 450, 500, 550, 600, 650, 700, 750, 800, 850, 900, 950, 1000, 1050, 1100, 1150, 1200, 1250, 1300, 1350 or more amino acids in length.

By "variants" is intended proteins or polypeptides having an amino acid sequence that is at least about 60%, 65%, about 70%, 75%, about 80%, 85%, about 90%, 91%, 92%, 93%, 94%, 95%, 96%, 97%, 98% or 99% identical to the amino acid sequence of any of SEQ ID NO:3-6. Variants also include polypeptides encoded by a nucleic acid molecule that hybridizes to the nucleic acid molecule of SEQ ID NO:1 or 2, or a complement thereof, under stringent conditions. Variants include polypeptides that differ in amino acid sequence due to mutagenesis. Variant proteins encompassed by the present invention are biologically active, that is they continue to possess the desired biological activity of the native protein, that is, retaining pesticidal activity. In some embodiments, the variants have improved activity relative to the native protein. Methods for measuring pesticidal activity are well known in the art. See, for example, Czapla and Lang (1990) *J. Econ. Entomol.* 83:2480-2485; Andrews et al. (1988) *Biochem. J.* 252:199-206; Marrone et al. (1985) *J. of Economic Entomology* 78:290-293; and U.S. Pat. No. 5,743,477, all of which are herein incorporated by reference in their entirety.

Bacterial genes, such as the axmi genes of this invention, quite often possess multiple methionine initiation codons in proximity to the start of the open reading frame. Often, translation initiation at one or more of these start codons will lead to generation of a functional protein. These start codons can include ATG codons. However, bacteria such as *Bacillus* sp. also recognize the codon GTG as a start codon, and proteins that initiate translation at GTG codons contain a methionine at the first amino acid. On rare occasions, translation in bacterial systems can initiate at a TTG codon, though in this event the TTG encodes a methionine. Furthermore, it is not often determined α priori which of these codons are used naturally in the bacterium. Thus, it is understood that use of one of the alternate methionine codons may also lead to generation of pesticidal proteins. These pesticidal proteins are encompassed in the present invention and may be used in the methods of the present invention. It will be understood that, when expressed in plants, it will be necessary to alter the alternate start codon to ATG for proper translation.

In various embodiments of the present invention, pesticidal proteins include amino acid sequences deduced from the full-length nucleotide sequences disclosed herein, and amino acid sequences that are shorter than the full-length sequences due to the use of an alternate downstream start site. Thus, the nucleotide sequence of the invention and/or vectors, host cells, and plants comprising the nucleotide sequence of the invention (and methods of making and using the nucleotide sequence of the invention) may comprise a nucleotide sequence encoding an amino acid sequence corresponding to SEQ ID NO:3, 4, or 5.

Antibodies to the polypeptides of the present invention, or to variants or fragments thereof, are also encompassed. Methods for producing antibodies are well known in the art (see, for example, Harlow and Lane (1988) *Antibodies: A Laboratory Manual*, Cold Spring Harbor Laboratory, Cold Spring Harbor, N.Y.; U.S. Pat. No. 4,196,265).

Thus, one aspect of the invention concerns antibodies, single-chain antigen binding molecules, or other proteins that specifically bind to one or more of the protein or peptide molecules of the invention and their homologs, fusions or fragments. In a particularly preferred embodiment, the antibody specifically binds to a protein having the amino acid sequence set forth in SEQ ID NO:3-6 or a fragment thereof. In another embodiment, the antibody specifically binds to a fusion protein comprising an amino acid sequence selected from the amino acid sequence set forth in SEQ ID NO:3-6 or a fragment thereof. In various embodiments, the antibody that specifically binds to the protein of the invention or a fusion protein comprising the protein of the invention is a non-naturally occurring antibody.

Antibodies of the invention may be used to quantitatively or qualitatively detect the protein or peptide molecules of the invention, or to detect post translational modifications of the proteins. As used herein, an antibody or peptide is said to "specifically bind" to a protein or peptide molecule of the invention if such binding is not competitively inhibited by the presence of non-related molecules.

The antibodies of the invention may be contained within a kit useful for detection of the protein or peptide molecules of the invention. The invention further comprises a method of detecting the protein or peptide molecule of the invention (particularly a protein encoded by the amino acid sequence set forth in SEQ ID NO:3-6, including variants or fragments thereof that are capable of specifically binding to the antibody of the invention) comprising contacting a sample with the antibody of the invention and determining whether the sample contains the protein or peptide molecule of the invention. Methods for utilizing antibodies for the detection of a protein or peptide of interest are known in the art.

Altered or Improved Variants

It is recognized that DNA sequences of a pesticidal protein may be altered by various methods, and that these alterations may result in DNA sequences encoding proteins with amino acid sequences different than that encoded by a pesticidal protein of the present invention. This protein may be altered in various ways including amino acid substitutions, deletions, truncations, and insertions of one or more amino acids of SEQ ID NO:3-6, including up to about 2, about 3, about 4, about 5, about 6, about 7, about 8, about 9, about 10, about 15, about 20, about 25, about 30, about 35, about 40, about 45, about 50, about 55, about 60, about 65, about 70, about 75, about 80, about 85, about 90, about 100, about 105, about 110, about 115, about 120, about 125, about 130, about 135, about 140, about 145, about 150, about 155, or more amino acid substitutions, deletions or insertions. Methods for such manipulations are generally known in the art. For example, amino acid sequence variants of a pesticidal protein can be prepared by mutations in the DNA. This may also be accomplished by one of several forms of mutagenesis and/or in directed evolution. In some aspects, the changes encoded in the amino acid sequence will not substantially affect the function of the protein. Such variants will possess the desired pesticidal activity. However, it is understood that the ability of a pesticidal protein to confer pesticidal activity may be improved by the use of such techniques upon the compositions of this invention. For example, one may express a pesticidal protein in host cells that exhibit high rates of base misincorporation during DNA replication, such as XL–1 Red (Stratagene, La Jolla, Calif.). After propagation in such strains, one can isolate the DNA (for example by preparing plasmid DNA, or by amplifying by PCR and cloning the resulting PCR fragment into a vector), culture the pesticidal protein mutations in a non-mutagenic strain, and identify mutated genes with pesticidal activity, for example by performing an assay to test for pesticidal activity. Generally, the protein is mixed and used in feeding assays. See, for example Marrone et al. (1985) *J. of Economic Entomology* 78:290-293. Such assays can include contacting plants with one or more pests and determining the plant's ability to survive and/or cause the death of the pests. Examples of mutations that result in increased toxicity are found in Schnepf et al. (1998) *Microbiol. Mol. Biol. Rev.* 62:775-806.

Alternatively, alterations may be made to the protein sequence of many proteins at the amino or carboxy terminus without substantially affecting activity. This can include insertions, deletions, or alterations introduced by modern molecular methods, such as PCR, including PCR amplifications that alter or extend the protein coding sequence by virtue of inclusion of amino acid encoding sequences in the oligonucleotides utilized in the PCR amplification. Alternatively, the protein sequences added can include entire protein-coding sequences, such as those used commonly in the art to generate protein fusions. Such fusion proteins are often used to (1) increase expression of a protein of interest (2) introduce a binding domain, enzymatic activity, or epitope to facilitate either protein purification, protein detection, or other experimental uses known in the art (3) target secretion or translation of a protein to a subcellular organelle, such as the periplasmic space of Gram-negative bacteria, or the endoplasmic reticulum of eukaryotic cells, the latter of which often results in glycosylation of the protein.

Variant nucleotide and amino acid sequences of the present invention also encompass sequences derived from mutagenic and recombinogenic procedures such as DNA shuffling. With such a procedure, one or more different pesticidal protein coding regions can be used to create a new pesticidal protein possessing the desired properties. In this manner, libraries of recombinant polynucleotides are generated from a population of related sequence polynucleotides comprising sequence regions that have substantial sequence identity and can be homologously recombined in vitro or in vivo. For example, using this approach, sequence motifs encoding a domain of interest may be shuffled between a pesticidal gene of the invention and other known pesticidal genes to obtain a new gene coding for a protein with an improved property of interest, such as an increased insecticidal activity. Strategies for such DNA shuffling are known in the art. See, for example, Stemmer (1994) *Proc. Natl. Acad. Sci. USA* 91:10747-10751; Stemmer (1994) *Nature* 370:389-391; Crameri et al. (1997) *Nature Biotech.* 15:436-438; Moore et al. (1997) *J. Mol. Biol.* 272:336-347; Zhang et al. (1997) *Proc. Natl. Acad. Sci. USA* 94:4504-4509; Crameri et al. (1998) *Nature* 391:288-291; and U.S. Pat. Nos. 5,605,793 and 5,837,458.

Domain swapping or shuffling is another mechanism for generating altered pesticidal proteins. Domains may be swapped between pesticidal proteins, resulting in hybrid or chimeric toxins with improved pesticidal activity or target spectrum. Methods for generating recombinant proteins and testing them for pesticidal activity are well known in the art (see, for example, Naimov et al. (2001) *Appl. Environ. Microbiol.* 67:5328-5330; de Maagd et al. (1996) *Appl. Environ. Microbiol.* 62:1537-1543; Ge et al. (1991) *J. Biol. Chem.* 266:17954-17958; Schnepf et al. (1990) *J. Biol. Chem.* 265:20923-20930; Rang et al. 91999) *Appl. Environ. Microbiol.* 65:2918-2925).

Vectors

A pesticidal sequence of the invention may be provided in an expression cassette for expression in a host cell of interest, e.g. a plant cell or a microbe. By "plant expression cassette" is intended a DNA construct that is capable of resulting in the expression of a protein from an open reading frame in a plant cell. Typically these contain a promoter and a coding sequence. Often, such constructs will also contain a 3' untranslated region. Such constructs may contain a "signal sequence" or "leader sequence" to facilitate co-translational or post-translational transport of the peptide to certain intracellular structures such as the chloroplast (or other plastid), endoplasmic reticulum, or Golgi apparatus.

By "signal sequence" is intended a sequence that is known or suspected to result in cotranslational or post-translational peptide transport across the cell membrane. In eukaryotes, this typically involves secretion into the Golgi apparatus, with some resulting glycosylation. Insecticidal toxins of bacteria are often synthesized as protoxins, which are protolytically activated in the gut of the target pest (Chang (1987) *Methods Enzymol.* 153:507-516). In some embodiments of the present invention, the signal sequence is located in the native sequence, or may be derived from a sequence of the invention. By "leader sequence" is intended any sequence that when translated, results in an amino acid sequence sufficient to trigger co-translational transport of the peptide chain to a subcellular organelle. Thus, this includes leader sequences targeting transport and/or glycosylation by passage into the endoplasmic reticulum, passage to vacuoles, plastids including chloroplasts, mitochondria, and the like. Thus, further provided herein is a polypeptide comprising an amino acid sequence of the present invention that is operably linked to a heterologous leader or signal sequence.

By "plant transformation vector" is intended a DNA molecule that is necessary for efficient transformation of a plant cell. Such a molecule may consist of one or more plant expression cassettes, and may be organized into more than one "vector" DNA molecule. For example, binary vectors are plant transformation vectors that utilize two non-contiguous DNA vectors to encode all requisite cis- and trans-acting functions for transformation of plant cells (Hellens and Mullineaux (2000) *Trends in Plant Science* 5:446-451). "Vector" refers to a nucleic acid construct designed for transfer between different host cells. "Expression vector" refers to a vector that has the ability to incorporate, integrate and express heterologous DNA sequences or fragments in a foreign cell. The cassette will include 5' and/or 3' regulatory sequences operably linked to a sequence of the invention. By "operably linked" is intended a functional linkage between a promoter and a second sequence, wherein the promoter sequence initiates and mediates transcription of the DNA sequence corresponding to the second sequence. Generally, operably linked means that the nucleic acid sequences being linked are contiguous and, where necessary to join two protein coding regions, contiguous and in the same reading frame. The cassette may additionally contain at least one additional gene to be cotransformed into the organism. Alternatively, the additional gene(s) can be provided on multiple expression cassettes.

In various embodiments, the nucleotide sequence of the invention is operably linked to a heterologous promoter capable of directing expression of the nucleotide sequence in a cell, e.g., a in a plant cell or a microbe. "Promoter" refers to a nucleic acid sequence that functions to direct transcription of a downstream coding sequence. The promoter together with other transcriptional and translational regulatory nucleic acid sequences (also termed "control sequences") are necessary for the expression of a DNA sequence of interest.

Such an expression cassette is provided with a plurality of restriction sites for insertion of the pesticidal sequence to be under the transcriptional regulation of the regulatory regions.

The expression cassette will include in the 5'-3' direction of transcription, a transcriptional and translational initiation region (i.e., a promoter), a DNA sequence of the invention, and a translational and transcriptional termination region (i.e., termination region) functional in plants. The promoter may be native or analogous, or foreign or heterologous, to the plant host and/or to the DNA sequence of the invention. Additionally, the promoter may be the natural sequence or alternatively a synthetic sequence. Where the promoter is "native" or "homologous" to the plant host, it is intended that the promoter is found in the native plant into which the promoter is introduced. Where the promoter is "foreign" or "heterologous" to the DNA sequence of the invention, it is intended that the promoter is not the native or naturally occurring promoter for the operably linked DNA sequence of the invention.

The termination region may be native with the transcriptional initiation region, may be native with the operably linked DNA sequence of interest, may be native with the plant host, or may be derived from another source (i.e., foreign or heterologous to the promoter, the DNA sequence of interest, the plant host, or any combination thereof). Convenient termination regions are available from the Ti-plasmid of *A. tumefaciens*, such as the octopine synthase and nopaline synthase termination regions. See also Guerineau et al. (1991) *Mol. Gen. Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) *Gene* 91:151-158; Ballas et al. (1989) *Nucleic Acids Res.* 17:7891-7903; and Joshi et al. (1987) *Nucleic Acid Res.* 15:9627-9639.

Where appropriate, the gene(s) may be optimized for increased expression in the transformed host cell. That is, the genes can be synthesized using host cell-preferred codons for improved expression, or may be synthesized using codons at a host-preferred codon usage frequency. Generally, the GC content of the gene will be increased. See, for example, Campbell and Gowri (1990) *Plant Physiol.* 92:1-11 for a discussion of host-preferred codon usage. Methods are available in the art for synthesizing plant-preferred genes. See, for example, U.S. Pat. Nos. 5,380,831, and 5,436,391, U.S. Patent Publication No. 20090137409, and Murray et al. (1989) *Nucleic Acids Res.* 17:477-498, herein incorporated by reference.

In one embodiment, the pesticidal protein is targeted to the chloroplast for expression. In this manner, where the pesticidal protein is not directly inserted into the chloroplast, the expression cassette will additionally contain a nucleic acid encoding a transit peptide to direct the pesticidal protein to the chloroplasts. Such transit peptides are known in the art. See, for example, Von Heijne et al. (1991) *Plant Mol. Biol. Rep.* 9:104-126; Clark et al. (1989) *J. Biol. Chem.* 264:17544-17550; Della-Cioppa et al. (1987) *Plant Physiol.* 84:965-968; Romer et al. (1993) *Biochem. Biophys. Res. Commun.* 196:1414-1421; and Shah et al. (1986) *Science* 233:478-481.

The pesticidal gene to be targeted to the chloroplast may be optimized for expression in the chloroplast to account for differences in codon usage between the plant nucleus and this organelle. In this manner, the nucleic acids of interest may be synthesized using chloroplast-preferred codons. See, for example, U.S. Pat. No. 5,380,831, herein incorporated by reference.

Plant Transformation

Methods of the invention involve introducing a nucleotide construct into a plant. By "introducing" is intended to present to the plant the nucleotide construct in such a manner that the construct gains access to the interior of a cell of the plant. The methods of the invention do not require that a particular method for introducing a nucleotide construct to a plant is used, only that the nucleotide construct gains access to the interior of at least one cell of the plant. Methods for introducing nucleotide constructs into plants are known in the art including, but not limited to, stable transformation methods, transient transformation methods, and virus-mediated methods.

By "plant" is intended whole plants, plant organs (e.g., leaves, stems, roots, etc.), seeds, plant cells, propagules, embryos and progeny of the same. Plant cells can be differentiated or undifferentiated (e.g. callus, suspension culture cells, protoplasts, leaf cells, root cells, phloem cells, pollen).

"Transgenic plants" or "transformed plants" or "stably transformed" plants or cells or tissues refers to plants that have incorporated or integrated exogenous nucleic acid sequences or DNA fragments into the plant cell. These nucleic acid sequences include those that are exogenous, or not present in the untransformed plant cell, as well as those that may be endogenous, or present in the untransformed plant cell. "Heterologous" generally refers to the nucleic acid sequences that are not endogenous to the cell or part of the native genome in which they are present, and have been added to the cell by infection, transfection, microinjection, electroporation, microproj ection, or the like.

The transgenic plants of the invention express one or more of the novel toxin sequences disclosed herein. In various embodiments, the transgenic plant further comprises one or more additional genes for insect resistance (e.g., Cry1, such as members of the Cry1A, Cry1B, Cry1C, Cry1D, Cry1E, and Cry1F families; Cry2, such as members of the Cry2A family; Cry9, such as members of the Cry9A, Cry9B, Cry9C, Cry9D, Cry9E, and Cry9F families; etc.). It will be understood by one of skill in the art that the transgenic plant may comprise any gene imparting an agronomic trait of interest.

Transformation of plant cells can be accomplished by one of several techniques known in the art. The pesticidal gene of the invention may be modified to obtain or enhance expression in plant cells. Typically a construct that expresses such a protein would contain a promoter to drive transcription of the gene, as well as a 3' untranslated region to allow transcription termination and polyadenylation. The organization of such constructs is well known in the art. In some instances, it may be useful to engineer the gene such that the resulting peptide is secreted, or otherwise targeted within the plant cell. For example, the gene can be engineered to contain a signal peptide to facilitate transfer of the peptide to the endoplasmic reticulum. It may also be preferable to engineer the plant expression cassette to contain an intron, such that mRNA processing of the intron is required for expression.

Typically this "plant expression cassette" will be inserted into a "plant transformation vector". This plant transformation vector may be comprised of one or more DNA vectors needed for achieving plant transformation. For example, it is a common practice in the art to utilize plant transformation vectors that are comprised of more than one contiguous DNA segment. These vectors are often referred to in the art as "binary vectors." Binary vectors as well as vectors with helper plasmids are most often used for *Agrobacterium*-mediated transformation, where the size and complexity of DNA segments needed to achieve efficient transformation is quite large, and it is advantageous to separate functions onto separate DNA molecules. Binary vectors typically contain a plasmid vector that contains the cis-acting sequences required for T-DNA transfer (such as left border and right border), a selectable marker that is engineered to be capable of expression in a plant cell, and a "gene of interest" (a gene engineered to be capable of expression in a plant cell for which generation of transgenic plants is desired). Also present on this plasmid vector are sequences required for bacterial replication. The cis-acting sequences are arranged in a fashion to allow efficient transfer into plant cells and expression therein. For example, the selectable marker gene and the pesticidal gene are located between the left and right borders. Often a second plasmid vector contains the trans-acting factors that mediate T-DNA transfer from *Agrobacterium* to plant cells. This plasmid often contains the virulence functions (Vir genes) that allow infection of plant cells by *Agrobacterium*, and transfer of DNA by cleavage at border sequences and vir-mediated DNA transfer, as is understood in the art (Hellens and Mullineaux (2000) *Trends in Plant Science* 5:446-451). Several types of *Agrobacte*-

*rium* strains (e.g. LBA4404, GV3101, EHA101, EHA105, etc.) can be used for plant transformation. The second plasmid vector is not necessary for transforming the plants by other methods such as microprojection, microinjection, electroporation, polyethylene glycol, etc.

In general, plant transformation methods involve transferring heterologous DNA into target plant cells (e.g. immature or mature embryos, suspension cultures, undifferentiated callus, protoplasts, etc.), followed by applying a maximum threshold level of appropriate selection (depending on the selectable marker gene) to recover the transformed plant cells from a group of untransformed cell mass. Explants are typically transferred to a fresh supply of the same medium and cultured routinely. Subsequently, the transformed cells are differentiated into shoots after placing on regeneration medium supplemented with a maximum threshold level of selecting agent. The shoots are then transferred to a selective rooting medium for recovering rooted shoot or plantlet. The transgenic plantlet then grows into a mature plant and produces fertile seeds (e.g. Hiei et al. (1994) *The Plant Journal* 6:271-282; Ishida et al. (1996) *Nature Biotechnology* 14:745-750). Explants are typically transferred to a fresh supply of the same medium and cultured routinely. A general description of the techniques and methods for generating transgenic plants are found in Ayres and Park (1994) *Critical Reviews in Plant Science* 13:219-239 and Bommineni and Jauhar (1997) *Maydica* 42:107-120. Since the transformed material contains many cells; both transformed and non-transformed cells are present in any piece of subjected target callus or tissue or group of cells. The ability to kill non-transformed cells and allow transformed cells to proliferate results in transformed plant cultures. Often, the ability to remove non-transformed cells is a limitation to rapid recovery of transformed plant cells and successful generation of transgenic plants.

Transformation protocols as well as protocols for introducing nucleotide sequences into plants may vary depending on the type of plant or plant cell, i.e., monocot or dicot, targeted for transformation. Generation of transgenic plants may be performed by one of several methods, including, but not limited to, microinjection, electroporation, direct gene transfer, introduction of heterologous DNA by *Agrobacterium* into plant cells (*Agrobacterium*-mediated transformation), bombardment of plant cells with heterologous foreign DNA adhered to particles, ballistic particle acceleration, aerosol beam transformation (U.S. Published Application No. 20010026941; U.S. Pat. No. 4,945,050; International Publication No. WO 91/00915; U.S. Published Application No. 2002015066), Lec1 transformation, and various other non-particle direct-mediated methods to transfer DNA.

Methods for transformation of chloroplasts are known in the art. See, for example, Svab et al. (1990) *Proc. Natl. Acad. Sci. USA* 87:8526-8530; Svab and Maliga (1993) *Proc. Natl. Acad. Sci. USA* 90:913-917; Svab and Maliga (1993) *EMBO J.* 12:601-606. The method relies on particle gun delivery of DNA containing a selectable marker and targeting of the DNA to the plastid genome through homologous recombination. Additionally, plastid transformation can be accomplished by transactivation of a silent plastid-borne transgene by tissue-preferred expression of a nuclear-encoded and plastid-directed RNA polymerase. Such a system has been reported in McBride et al. (1994) *Proc. Natl. Acad. Sci. USA* 91:7301-7305.

Following integration of heterologous foreign DNA into plant cells, one then applies a maximum threshold level of appropriate selection in the medium to kill the untransformed cells and separate and proliferate the putatively transformed cells that survive from this selection treatment by transferring regularly to a fresh medium. By continuous passage and challenge with appropriate selection, one identifies and proliferates the cells that are transformed with the plasmid vector. Molecular and biochemical methods can then be used to confirm the presence of the integrated heterologous gene of interest into the genome of the transgenic plant.

The cells that have been transformed may be grown into plants in accordance with conventional ways. See, for example, McCormick et al. (1986) *Plant Cell Reports* 5:81-84. These plants may then be grown, and either pollinated with the same transformed strain or different strains, and the resulting hybrid having constitutive expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved. In this manner, the present invention provides transformed seed (also referred to as "transgenic seed") having a nucleotide construct of the invention, for example, an expression cassette of the invention, stably incorporated into their genome.

Evaluation of Plant Transformation

Following introduction of heterologous foreign DNA into plant cells, the transformation or integration of heterologous gene in the plant genome is confirmed by various methods such as analysis of nucleic acids, proteins and metabolites associated with the integrated gene.

PCR analysis is a rapid method to screen transformed cells, tissue or shoots for the presence of incorporated gene at the earlier stage before transplanting into the soil (Sambrook and Russell (2001) *Molecular Cloning: A Laboratory Manual.* Cold Spring Harbor Laboratory Press, Cold Spring Harbor, N.Y.). PCR is carried out using oligonucleotide primers specific to the gene of interest or *Agrobacterium* vector background, etc.

Plant transformation may be confirmed by Southern blot analysis of genomic DNA (Sambrook and Russell, 2001, supra). In general, total DNA is extracted from the transformant, digested with appropriate restriction enzymes, fractionated in an agarose gel and transferred to a nitrocellulose or nylon membrane. The membrane or "blot" is then probed with, for example, radiolabeled $^{32}$P target DNA fragment to confirm the integration of introduced gene into the plant genome according to standard techniques (Sambrook and Russell, 2001, supra).

In Northern blot analysis, RNA is isolated from specific tissues of transformant, fractionated in a formaldehyde agarose gel, and blotted onto a nylon filter according to standard procedures that are routinely used in the art (Sambrook and Russell, 2001, supra). Expression of RNA encoded by the pesticidal gene is then tested by hybridizing the filter to a radioactive probe derived from a pesticidal gene, by methods known in the art (Sambrook and Russell, 2001, supra).

Western blot, biochemical assays and the like may be carried out on the transgenic plants to confirm the presence of protein encoded by the pesticidal gene by standard procedures (Sambrook and Russell, 2001, supra) using antibodies that bind to one or more epitopes present on the pesticidal protein.

Pesticidal Activity in Plants

In another aspect of the invention, one may generate transgenic plants expressing a pesticidal protein that has pesticidal activity. Methods described above by way of example may be utilized to generate transgenic plants, but the manner in which the transgenic plant cells are generated is not critical to this invention. Methods known or described in the art such as *Agrobacterium*-mediated transformation, biolistic transformation, and non-particle-mediated methods may be used at the discretion of the experimenter. Plants expressing a pesticidal protein may be isolated by common methods described in the art, for example by transformation of callus, selection of transformed callus, and regeneration of fertile plants from such transgenic callus. In such process, one may use any gene as a selectable marker so long as its expression in plant cells confers ability to identify or select for transformed cells.

A number of markers have been developed for use with plant cells, such as resistance to chloramphenicol, the aminoglycoside G418, hygromycin, or the like. Other genes that encode a product involved in chloroplast metabolism may also be used as selectable markers. For example, genes that provide resistance to plant herbicides such as glyphosate, bromoxynil, or imidazolinone may find particular use. Such genes have been reported (Stalker et al. (1985) *J. Biol. Chem.* 263:6310-6314 (bromoxynil resistance nitrilase gene); and Sathasivan et al. (1990) *Nucl. Acids Res.* 18:2188 (AHAS imidazolinone resistance gene). Additionally, the genes disclosed herein are useful as markers to assess transformation of bacterial or plant cells. Methods for detecting the presence of a transgene in a plant, plant organ (e.g., leaves, stems, roots, etc.), seed, plant cell, propagule, embryo or progeny of the same are well known in the art. In one embodiment, the presence of the transgene is detected by testing for pesticidal activity.

Fertile plants expressing a pesticidal protein may be tested for pesticidal activity, and the plants showing optimal activity selected for further breeding. Methods are available in the art to assay for pest activity. Generally, the protein is mixed and used in feeding assays. See, for example Marrone et al. (1985) *J. of Economic Entomology* 78:290-293.

The present invention may be used for transformation of any plant species, including, but not limited to, monocots and dicots. Examples of plants of interest include, but are not limited to, corn (maize), sorghum, wheat, sunflower, tomato, crucifers, peppers, potato, cotton, rice, soybean, sugarbeet, sugarcane, tobacco, barley, and oilseed rape, *Brassica* sp., alfalfa, rye, millet, safflower, peanuts, sweet potato, cassava, coffee, coconut, pineapple, citrus trees, cocoa, tea, banana, avocado, fig, guava, mango, olive, papaya, cashew, macadamia, almond, oats, vegetables, ornamentals, and conifers. Vegetables include, but are not limited to, tomatoes, lettuce, green beans, lima beans, peas, and members of the genus Curcumis such as cucumber, cantaloupe, and musk melon. Ornamentals include, but are not limited to, azalea, hydrangea, hibiscus, roses, tulips, daffodils, petunias, carnation, poinsettia, and chrysanthemum. Preferably, plants of the present invention are crop plants (for example, maize, sorghum, wheat, sunflower, tomato, crucifers, peppers, potato, cotton, rice, soybean, sugarbeet, sugarcane, tobacco, barley, oilseed rape., etc.).

Use in Pesticidal Control

General methods for employing strains comprising a nucleotide sequence of the present invention, or a variant thereof, in pest control or in engineering other organisms as pesticidal agents are known in the art. See, for example U.S. Pat. No. 5,039,523 and EP 0480762A2.

The *Bacillus* strains containing a nucleotide sequence of the present invention, or a variant thereof, or the microorganisms that have been genetically altered to contain a pesticidal gene of the invention and protein may be used for protecting agricultural crops and products from pests. In one aspect of the invention, whole, i.e., unlysed, cells of a toxin (pesticide)-producing organism are treated with reagents that prolong the activity of the toxin produced in the cell when the cell is applied to the environment of target pest(s).

Alternatively, the pesticide is produced by introducing a pesticidal gene into a cellular host. Expression of the pesticidal gene results, directly or indirectly, in the intracellular production and maintenance of the pesticide. In one aspect of this invention, these cells are then treated under conditions that prolong the activity of the toxin produced in the cell when the cell is applied to the environment of the target pest(s). The resulting product retains the toxicity of the toxin. These naturally encapsulated pesticides may then be formulated in accordance with conventional techniques for application to the environment hosting a target pest, e.g., soil, water, and foliage of plants. See, for example EPA 0192319, and the references cited therein. Alternatively, one may formulate the cells expressing a gene of this invention such as to allow application of the resulting material as a pesticide.

The active ingredients of the present invention are normally applied in the form of compositions and can be applied to the crop area or plant to be treated, simultaneously or in succession, with other compounds. These compounds can be fertilizers, weed killers, cryoprotectants, surfactants, detergents, pesticidal soaps, dormant oils, polymers, and/or time-release or biodegradable carrier formulations that permit long-term dosing of a target area following a single application of the formulation. They can also be selective herbicides, chemical insecticides, virucides, microbicides, amoebicides, pesticides, fungicides, bacteriocides, nematocides, molluscicides or mixtures of several of these preparations, if desired, together with further agriculturally acceptable carriers, surfactants or application-promoting adjuvants customarily employed in the art of formulation. Suitable carriers and adjuvants can be solid or liquid and correspond to the substances ordinarily employed in formulation technology, e.g. natural or regenerated mineral substances, solvents, dispersants, wetting agents, tackifiers, binders or fertilizers. Likewise the formulations may be prepared into edible "baits" or fashioned into pest "traps" to permit feeding or ingestion by a target pest of the pesticidal formulation.

Methods of applying an active ingredient of the present invention or an agrochemical composition of the present invention that contains at least one of the pesticidal proteins produced by the bacterial strains of the present invention include leaf application, seed coating and soil application. The number of applications and the rate of application depend on the intensity of infestation by the corresponding pest.

The composition may be formulated as a powder, dust, pellet, granule, spray, emulsion, colloid, solution, or such like, and may be prepared by such conventional means as desiccation, lyophilization, homogenation, extraction, filtration, centrifugation, sedimentation, or concentration of a culture of cells comprising the polypeptide. In all such compositions that contain at least one such pesticidal polypeptide, the polypeptide may be present in a concentration of from about 1% to about 99% by weight.

Lepidopteran, hemipteran, dipteran, or coleopteran pests may be killed or reduced in numbers in a given area by the methods of the invention, or may be prophylactically applied to an environmental area to prevent infestation by a susceptible pest. Preferably the pest ingests, or is contacted with, a pesticidally-effective amount of the polypeptide. By "pesticidally-effective amount" is intended an amount of the pesticide that is able to bring about death to at least one pest, or to noticeably reduce pest growth, feeding, or normal physiological development. This amount will vary depending on such factors as, for example, the specific target pests to be controlled, the specific environment, location, plant, crop, or agricultural site to be treated, the environmental conditions, and the method, rate, concentration, stability, and quantity of application of the pesticidally-effective polypeptide composition. The formulations may also vary with respect to climatic conditions, environmental considerations, and/or frequency of application and/or severity of pest infestation.

The pesticide compositions described may be made by formulating either the bacterial cell, the crystal and/or the spore suspension, or the isolated protein component with the desired agriculturally-acceptable carrier. The compositions may be formulated prior to administration in an appropriate means such as lyophilized, freeze-dried, desiccated, or in an aqueous carrier, medium or suitable diluent, such as saline or other buffer. The formulated compositions may be in the form of a dust or granular material, or a suspension in oil (vegetable or mineral), or water or oil/water emulsions, or as a wettable powder, or in combination with any other carrier material suitable for agricultural application. Suitable agricultural carriers can be solid or liquid and are well known in the art. The term "agriculturally-acceptable carrier" covers all adjuvants, inert components, dispersants, surfactants, tackifiers, binders, etc. that are ordinarily used in pesticide formulation technology; these are well known to those skilled in pesticide formulation. The formulations may be mixed with one or more solid or liquid adjuvants and prepared by various means, e.g., by homogeneously mixing, blending and/or grinding the pesticidal composition with suitable adjuvants using conventional formulation techniques. Suitable formulations and application methods are described in U.S. Pat. No. 6,468,523, herein incorporated by reference.

"Pest" includes but is not limited to, insects, fungi, bacteria, nematodes, mites, ticks, and the like. Insect pests include insects selected from the orders Coleoptera, Diptera, Hymenoptera, Lepidoptera, Mallophaga, Homoptera, Hemiptera, Orthroptera, Thysanoptera, Dermaptera, Isoptera, Anoplura, Siphonaptera, Trichoptera, etc., particularly Coleoptera, Lepidoptera, and Diptera.

The order Coleoptera includes the suborders Adephaga and Polyphaga. Suborder Adephaga includes the superfamilies Caraboidea and Gyrinoidea, while suborder Polyphaga includes the superfamilies Hydrophiloidea, Staphylinoidea, Cantharoidea, Cleroidea, Elateroidea, Dascilloidea, Dryopoidea, Byrrhoidea, Cucujoidea, Meloidea, Mordelloidea, Tenebrionoidea, Bostrichoidea, Scarabaeoidea, Cerambycoidea, Chrysomeloidea, and Curculionoidea. Superfamily Caraboidea includes the families Cicindelidae, Carabidae, and Dytiscidae. Superfamily Gyrinoidea includes the family Gyrinidae. Superfamily Hydrophiloidea includes the family Hydrophilidae. Superfamily Staphylinoidea includes the families Silphidae and Staphylinidae. Superfamily Cantharoidea includes the families Cantharidae and Lampyridae. Superfamily Cleroidea includes the families Cleridae and Dermestidae. Superfamily Elateroidea includes the families Elateridae and Buprestidae. Superfamily Cucujoidea includes the family Coccinellidae. Superfamily Meloidea includes the family Meloidae. Superfamily Tenebrionoidea includes the family Tenebrionidae. Superfamily Scarabaeoidea includes the families Passalidae and Scarabaeidae. Superfamily Cerambycoidea includes the family Cerambycidae. Superfamily Chrysomeloidea includes the family Chrysomelidae. Superfamily Curculionoidea includes the families Curculionidae and Scolytidae.

The order Diptera includes the Suborders Nematocera, Brachycera, and Cyclorrhapha. Suborder Nematocera includes the families Tipulidae, Psychodidae, Culicidae, Ceratopogonidae, Chironomidae, Simuliidae, Bibionidae, and Cecidomyiidae. Suborder Brachycera includes the families Stratiomyidae, Tabanidae, Therevidae, Asilidae, Mydidae, Bombyliidae, and Dolichopodidae. Suborder Cyclorrhapha includes the Divisions Aschiza and Aschiza. Division Aschiza includes the families Phoridae, Syrphidae, and Conopidae. Division Aschiza includes the Sections Acalyptratae and Calyptratae. Section Acalyptratae includes the families Otitidae, Tephritidae, Agromyzidae, and Drosophilidae. Section Calyptratae includes the families Hippoboscidae, Oestridae, Tachinidae, Anthomyiidae, Muscidae, Calliphoridae, and Sarcophagidae.

The order Lepidoptera includes the families Papilionidae, Pieridae, Lycaenidae, Nymphalidae, Danaidae, Satyridae, Hesperiidae, Sphingidae, Saturniidae, Geometridae, Arctiidae, Noctuidae, Lymantriidae, Sesiidae, and Tineidae.

Insect pests of the invention for the major crops include: Maize: *Ostrinia nubilalis*, European corn borer; *Agrotis ipsilon*, black cutworm; *Helicoverpa zea*, corn earworm; *Spodoptera frugiperda*, fall armyworm; *Diatraea grandiosella*, southwestern corn borer; *Elasmopalpus lignosellus*, lesser cornstalk borer; *Diatraea saccharalis*, surgarcane borer; *Diabrotica virgifera*, western corn rootworm; *Diabrotica longicornis barberi*, northern corn rootworm; *Diabrotica undecimpunctata howardi*, southern corn rootworm; *Melanotus* spp., wireworms; *Cyclocephala borealis*, northern masked chafer (white grub); *Cyclocephala immaculata*, southern masked chafer (white grub); *Popillia japonica*, Japanese beetle; *Chaetocnema pulicaria*, corn flea beetle; *Sphenophorus maidis*, maize billbug; *Rhopalosiphum maidis*, corn leaf aphid; *Anuraphis maidiradicis*, corn root aphid; *Blissus leucopterus leucopterus*, chinch bug; *Melanoplus femurrubrum*, redlegged grasshopper; *Melanoplus sanguinipes*, migratory grasshopper; *Hylemya platura*, seedcorn maggot; *Agromyza parvicornis*, corn blot leafminer; *Anaphothrips obscrurus*, grass thrips; *Solenopsis milesta*, thief ant; *Tetranychus urticae*, twospotted spider mite; Sorghum: *Chilo partellus*, sorghum borer; *Spodoptera frugiperda*, fall armyworm; *Helicoverpa zea*, corn earworm; *Elasmopalpus lignosellus*, lesser cornstalk borer; *Feltia subterranea*, granulate cutworm; *Phyllophaga crinita*, white grub; *Eleodes, Conoderus,* and *Aeolus* spp., wireworms; *Oulema melanopus*, cereal leaf beetle; *Chaetocnema pulicaria*, corn flea beetle; *Sphenophorus maidis*, maize billbug; *Rhopalosiphum maidis*; corn leaf aphid; *Sipha flava*, yellow sugarcane aphid; *Blissus leucopterus leucopterus*, chinch bug; *Contarinia sorghicola*, sorghum midge; *Tetranychus cinnabarinus*, carmine spider mite; *Tetranychus urticae*, twospotted spider mite; Wheat: *Pseudaletia unipunctata*, army worm; *Spodoptera frugiperda*, fall armyworm; *Elasmopalpus lignosellus*, lesser cornstalk borer; *Agrotis orthogonia*, western cutworm; *Elasmopalpus lignosellus*, lesser cornstalk borer; *Oulema melanopus*, cereal leaf beetle; *Hypera punctata*, clover leaf weevil; *Diabrotica undecimpunctata howardi*, southern corn rootworm; Russian wheat aphid; *Schizaphis graminum*, greenbug; *Macrosiphum avenae*, English grain aphid; *Melanoplus femurrubrum*, redlegged grasshopper; *Melanoplus differentialis*, differential grasshopper; *Melanoplus sanguinipes*, migratory grasshopper; *Mayetiola destructor*, Hessian fly; *Sitodiplosis mosellana*, wheat midge; *Meromyza americana*, wheat stem maggot; *Hylemya coarctate*, wheat bulb fly; *Frankliniella*

*fusca*, tobacco thrips; *Cephus cinctus*, wheat stem sawfly; *Aceria tulipae*, wheat curl mite; Sunflower: *Suleima helianthana*, sunflower bud moth; *Homoeosoma electellum*, sunflower moth; *zygogramma exclamationis*, sunflower beetle; *Bothyrus gibbosus*, carrot beetle; *Neolasioptera murtfeldtiana*, sunflower seed midge; Cotton: *Heliothis virescens*, cotton budworm; *Helicoverpa zea*, cotton bollworm; *Spodoptera exigua*, beet armyworm; *Pectinophora gossypiella*, pink bollworm; *Anthonomus grandis*, boll weevil; *Aphis gossypii*, cotton aphid; *Pseudatomoscelis seriatus*, cotton fleahopper; *Trialeurodes abutilonea*, bandedwinged whitefly; *Lygus lineolaris*, tarnished plant bug; *Melanoplus femurrubrum*, redlegged grasshopper; *Melanoplus differentialis*, differential grasshopper; *Thrips tabaci*, onion thrips; *Franklinkiella fusca*, tobacco thrips; *Tetranychus cinnabarinus*, carmine spider mite; *Tetranychus urticae*, twospotted spider mite; Rice: *Diatraea saccharalis*, sugarcane borer; *Spodoptera frugiperda*, fall armyworm; *Helicoverpa zea*, corn earworm; *Colaspis brunnea*, grape colaspis; *Lissorhoptrus oryzophilus*, rice water weevil; *Sitophilus oryzae*, rice weevil; *Nephotettix nigropictus*, rice leafhopper; *Blissus leucopterus leucopterus*, chinch bug; *Acrosternum hilare*, green stink bug; Soybean: *Pseudoplusia includens*, soybean looper; *Anticarsia gemmatalis*, velvetbean caterpillar; *Plathypena scabs*, green cloverworm; *Ostrinia nubilalis*, European corn borer; *Agrotis ipsilon*, black cutworm; *Spodoptera exigua*, beet armyworm; *Heliothis virescens*, cotton budworm; *Helicoverpa zea*, cotton bollworm; *Epilachna varivestis*, Mexican bean beetle; *Myzus persicae*, green peach aphid; *Empoasca fabae*, potato leafhopper; *Acrosternum hilare*, green stink bug; *Melanoplus femurrubrum*, redlegged grasshopper; *Melanoplus differentialis*, differential grasshopper; *Hylemya platura*, seedcorn maggot; *Sericothrips variabilis*, soybean thrips; *Thrips tabaci*, onion thrips; *Tetranychus turkestani*, strawberry spider mite; *Tetranychus urticae*, twospotted spider mite; Barley: *Ostrinia nubilalis*, European corn borer; *Agrotis ipsilon*, black cutworm; *Schizaphis graminum*, greenbug; *Blissus leucopterus leucopterus*, chinch bug; *Acrosternum hilare*, green stink bug; *Euschistus servus*, brown stink bug; *Delia platura*, seedcorn maggot; *Mayetiola destructor*, Hessian fly; *Petrobia latens*, brown wheat mite; Oil Seed Rape: *Brevicoryne brassicae*, cabbage aphid; *Phyllotreta cruciferae*, Flea beetle; *Mamestra configurata*, Bertha armyworm; *Plutella xylostella*, Diamond-back moth; *Delia* ssp., Root maggots.

Nematodes include parasitic nematodes such as root-knot, cyst, and lesion nematodes, including *Heterodera* spp., *Meloidogyne* spp., and *Globodera* spp.; particularly members of the cyst nematodes, including, but not limited to, *Heterodera glycines* (soybean cyst nematode); *Heterodera schachtii* (beet cyst nematode); *Heterodera avenae* (cereal cyst nematode); and *Globodera rostochiensis* and *Globodera pailida* (potato cyst nematodes). Lesion nematodes include *Pratylenchus* spp.

Methods for Increasing Plant Yield

Methods for increasing plant yield are provided. The methods comprise providing a plant or plant cell expressing a polynucleotide encoding the pesticidal polypeptide sequence disclosed herein and growing the plant or a seed thereof in a field infested with (or susceptible to infestation by) a pest against which said polypeptide has pesticidal activity. In some embodiments, the polypeptide has pesticidal activity against a lepidopteran, coleopteran, dipteran, hemipteran, or nematode pest, and said field is infested with a lepidopteran, hemipteran, coleopteran, dipteran, or nematode pest. As defined herein, the "yield" of the plant refers to the quality and/or quantity of biomass produced by the plant. By "biomass" is intended any measured plant product. An increase in biomass production is any improvement in the yield of the measured plant product. Increasing plant yield has several commercial applications. For example, increasing plant leaf biomass may increase the yield of leafy vegetables for human or animal consumption. Additionally, increasing leaf biomass can be used to increase production of plant-derived pharmaceutical or industrial products. An increase in yield can comprise any statistically significant increase including, but not limited to, at least a 1% increase, at least a 3% increase, at least a 5% increase, at least a 10% increase, at least a 20% increase, at least a 30%, at least a 50%, at least a 70%, at least a 100% or a greater increase in yield compared to a plant not expressing the pesticidal sequence. In specific methods, plant yield is increased as a result of improved pest resistance of a plant expressing a pesticidal protein disclosed herein. Expression of the pesticidal protein results in a reduced ability of a pest to infest or feed.

The plants can also be treated with one or more chemical compositions, including one or more herbicide, insecticides, or fungicides. Exemplary chemical compositions include: Fruits/Vegetables Herbicides: Atrazine, Bromacil, Diuron, Glyphosate, Linuron, Metribuzin, Simazine, Trifluralin, Fluazifop, Glufosinate, Halosulfuron Gowan, Paraquat, Propyzamide, Sethoxydim, Butafenacil, Halosulfuron, Indaziflam; Fruits/Vegetables Insecticides: Aldicarb, *Bacillus thuringiensis*, Carbaryl, Carbofuran, Chlorpyrifos, Cypermethrin, Deltamethrin, Abamectin, Cyfluthrin/beta-cyfluthrin, Esfenvalerate, Lambda-cyhalothrin, Acequinocyl, Bifenazate, Methoxyfenozide, Novaluron, Chromafenozide, Thiacloprid, Dinotefuran, Fluacrypyrim, Spirodiclofen, Gamma-cyhalothrin, Spiromesifen, Spinosad, Rynaxypyr, Cyazypyr, Triflumuron, Spirotetramat, Imidacloprid, Flubendiamide, Thiodicarb, Metaflumizone, Sulfoxaflor, Cyflumetofen, Cyanopyrafen, Clothianidin, Thiamethoxam, Spinotoram, Thiodicarb, Flonicamid, Methiocarb, Emamectin-benzoate, Indoxacarb, Fenamiphos, Pyriproxifen, Fenbutatin-oxid; Fruits/Vegetables Fungicides: Ametoctradin, Azoxystrobin, Benthiavalicarb, Boscalid, Captan, Carbendazim, Chlorothalonil, Copper, Cyazofamid, Cyflufenamid, Cymoxanil, Cyproconazole, Cyprodinil, Difenoconazole, Dimetomorph, Dithianon, Fenamidone, Fenhexamid, Fluazinam, Fludioxonil, Fluopicolide, Fluopyram, Fluoxastrobin, Fluxapyroxad, Folpet, Fosetyl, Iprodione, Iprovalicarb, Isopyrazam, Kresoxim-methyl, Mancozeb, Mandipropamid, Metalaxyl/mefenoxam, Metiram, Metrafenone, Myclobutanil, Penconazole, Penthiopyrad, Picoxystrobin, Propamocarb, Propiconazole, Propineb, Proquinazid, Prothioconazole, Pyraclostrobin, Pyrimethanil, Quinoxyfen, Spiroxamine, Sulphur, Tebuconazole, Thiophanate-methyl, Trifloxystrobin; Cereals Herbicides: 2.4-D, Amidosulfuron, Bromoxynil, Carfentrazone-E, Chlorotoluron, Chlorsulfuron, Clodinafop-P, Clopyralid, Dicamba, Diclofop-M, Diflufenican, Fenoxaprop, Florasulam, Flucarbazone-NA, Flufenacet, Flupyrosulfuron-M, Fluroxypyr, Flurtamone, Glyphosate, Iodosulfuron, Ioxynil, Isoproturon, MCPA, Mesosulfuron, Metsulfuron, Pendimethalin, Pinoxaden, Propoxycarbazone, Prosulfocarb, Pyroxsulam, Sulfosulfuron, Thifensulfuron, Tralkoxydim, Triasulfuron, Tribenuron, Trifluralin, Tritosulfuron; Cereals Fungicides: Azoxystrobin, Bixafen, Boscalid, Carbendazim, Chlorothalonil, Cyflufenamid, Cyproconazole, Cyprodinil, Dimoxystrobin, Epoxiconazole, Fenpropidin, Fenpropimorph, Fluoxapyr, Fluoxastrobin, Fluquinconazole, Fluxapyroxad, Isopyrazam, Kresoxim-methyl, Metconazole, Metrafenone, Penthiopyrad, Picoxystrobin, Prochloraz, Propiconazole, Proquinazid, Prothioconazole, Pyraclostrobin, Quinoxyfen, Spiroxamine, Tebuconazole, Thiophanate-methyl, Trifloxystrobin; Cereals Insecticides: Dimethoate, Lambda-cyhalthrin, Deltamethrin, alpha-Cypermethrin, ß-cyfluthrin, Bifenthrin, Imidacloprid, Clothianidin, Thiamethoxam, Thiacloprid, Acetamiprid, Dinetofuran, Clorphyriphos, Pirimicarb, Methiocarb, Sulfoxaflor; Maize Herbicides: Atrazine, Alachlor, Bromoxynil, Acetochlor, Dicamba, Clopyralid, (S-)Dimethenamid, Glufosinate, Glyphosate, Isoxaflutole, (S-)Metolachlor, Mesotrione, Nicosulfuron, Primisulfuron, Rimsulfuron, Sulcotrione, Foramsulfuron, Topramezone, Tembotrione, Saflufenacil, Thiencarbazone, Flufenacet, Pyroxasulfon; Maize Insecticides: Carbofuran, Chlorpyrifos, Bifenthrin, Fipronil, Imidacloprid, Lambda-Cyhalothrin, Tefluthrin, Terbufos, Thiamethoxam, Clothianidin, Spiromesifen, Flubendiamide, Triflumuron, Rynaxypyr, Deltamethrin, Thiodicarb, ß-Cyfluthrin, Cypermethrin, Bifenthrin, Lufenuron, Tebupirimphos, Ethiprole, Cyazypyr, Thiacloprid, Acetamiprid, Dinetofuran, Avermectin; Maize Fungicides: Azoxystrobin, Bixafen, Boscalid, Cyproconazole, Dimoxystrobin, Epoxiconazole, Fenitropan, Fluopyram, Fluoxastrobin, Fluxapyroxad, Isopyrazam, Metconazole, Penthiopyrad, Picoxystrobin, Propiconazole, Prothioconazole, Pyraclostrobin, Tebuconazole, Trifloxystrobin; Rice Herbicides: Butachlor, Propanil, Azimsulfuron, Bensulfuron, Cyhalofop, Daimuron, Fentrazamide, Imazosulfuron, Mefenacet, Oxaziclomefone, Pyrazosulfuron, Pyributicarb, Quinclorac, Thiobencarb, Indanofan, Flufenacet, Fentrazamide, Halosulfuron, Oxaziclomefone, Benzobicyclon, Pyriftalid, Penoxsulam, Bispyribac, Oxadiargyl, Ethoxysulfuron, Pretilachlor, Mesotrione, Tefuryltrione, Oxadiazone, Fenoxaprop, Pyrimisulfan; Rice Insecticides: Diazinon, Fenobucarb, Benfuracarb, Buprofezin, Dinotefuran, Fipronil, Imidacloprid, Isoprocarb, Thiacloprid, Chromafenozide, Clothianidin, Ethiprole, Flubendiamide, Rynaxypyr, Deltamethrin, Acetamiprid, Thiamethoxam, Cyazypyr, Spinosad, Spinotoram, Emamectin-Benzoate, Cypermethrin, Chlorpyriphos, Etofenprox, Carbofuran, Benfuracarb, Sulfoxaflor; Rice Fungicides: Azoxystrobin, Carbendazim, Carpropamid, Diclocymet, Difenoconazole, Edifenphos, Ferimzone, Gentamycin, Hexaconazole, Hymexazol, Iprobenfos (IBP), Isoprothiolane, Isotianil, Kasugamycin, Mancozeb, Metominostrobin, Orysastrobin, Pencycuron, Probenazole, Propiconazole, Propineb, Pyroquilon, Tebuconazole, Thiophanate-methyl, Tiadinil, Tricyclazole, Trifloxystrobin, Validamycin; Cotton Herbicides: Diuron, Fluometuron, MSMA, Oxyfluorfen, Prometryn, Trifluralin, Carfentrazone, Clethodim, Fluazifop-butyl, Glyphosate, Norflurazon, Pendimethalin, Pyrithiobac-sodium, Trifloxysulfuron, Tepraloxydim, Glufosinate, Flumioxazin, Thidiazuron; Cotton Insecticides: Acephate, Aldicarb, Chlorpyrifos, Cypermethrin, Deltamethrin, Abamectin, Acetamiprid, Emamectin Benzoate, Imidacloprid, Indoxacarb, Lambda-Cyhalothrin, Spinosad, Thiodicarb, Gamma-Cyhalothrin, Spiromesifen, Pyridalyl, Flonicamid Flubendiamide, Triflumuron, Rynaxypyr, Beta-Cyfluthrin, Spirotetramat, Clothianidin, Thiamethoxam, Thiacloprid, Dinetofuran, Flubendiamide, Cyazypyr, Spinosad, Spinotoram, gamma Cyhalothrin, 4-[[(6-Chlorpyridin-3-yl)methyl](2,2-difluorethyl)amino]furan-2(5H)-on, Thiodicarb, Avermectin, Flonicamid, Pyridalyl, Spiromesifen, Sulfoxaflor; Cotton Fungicides: Azoxystrobin, Bixafen, Boscalid, Carbendazim, Chlorothalonil, Copper, Cyproconazole, Difenoconazole, Dimoxystrobin, Epoxiconazole, Fenamidone, Fluazinam, Fluopyram, Fluoxastrobin, Fluxapyroxad, Iprodione, Isopyrazam, Isotianil, Mancozeb, Maneb, Metominostrobin, Penthiopyrad, Picoxystrobin, Propineb, Prothioconazole, Pyraclostrobin, Quintozene, Tebuconazole, Tetraconazole, Thiophanate-methyl, Trifloxystrobin; Soybean Herbicides: Alachlor, Bentazone, Trifluralin, Chlorimuron-Ethyl, Cloransulam-Methyl, Fenoxaprop, Fomesafen, Fluazifop, Glyphosate, Imazamox, Imazaquin, Imazethapyr, (S-)Metolachlor, Metribuzin, Pendimethalin, Tepraloxydim, Glufosinate; Soybean Insecticides: Lambda-cyhalothrin, Methomyl, Imidacloprid, Clothianidin, Thiamethoxam, Thiacloprid, Acetamiprid, Dinetofuran, Flubendiamide, Rynaxypyr, Cyazypyr, Spinosad, Spinotoram, Emamectin-Benzoate, Fipronil, Ethiprole, Deltamethrin, ß-Cyfluthrin, gamma and lambda Cyhalothrin, 4-[[(6-Chlorpyridin-3-yl)methyl](2,2-difluorethyl)amino]furan-2(5H)-on, Spirotetramat, Spinodiclofen, Triflumuron, Flonicamid, Thiodicarb, beta-Cyfluthrin; Soybean Fungicides: Azoxystrobin, Bixafen, Boscalid, Carbendazim, Chlorothalonil, Copper, Cyproconazole, Difenoconazole, Dimoxystrobin, Epoxiconazole, Fluazinam, Fluopyram, Fluoxastrobin, Flutriafol, Fluxapyroxad, Isopyrazam, Iprodione, Isotianil, Mancozeb, Maneb, Metconazole, Metominostrobin, Myclobutanil, Penthiopyrad, Picoxystrobin, Propiconazole, Propineb, Prothioconazole, Pyraclostrobin, Tebuconazole, Tetraconazole, Thiophanate-methyl, Trifloxystrobin; Sugarbeet Herbicides: Chloridazon, Desmedipham, Ethofumesate, Phenmedipham, Triallate, Clopyralid, Fluazifop, Lenacil, Metamitron, Quinmerac, Cycloxydim, Triflusulfuron, Tepraloxydim, Quizalofop; Sugarbeet Insecticides: Imidacloprid, Clothianidin, Thiamethoxam, Thiacloprid, Acetamiprid, Dinetofuran, Deltamethrin, ß-Cyfluthrin, gamma/lambda Cyhalothrin, 4-[[(6-Chlorpyridin-3-yl)methyl](2,2-difluorethyl)amino]furan-2 (5H)-on, Tefluthrin, Rynaxypyr, Cyaxypyr, Fipronil, Carbofuran; Canola Herbicides: Clopyralid, Diclofop, Fluazifop, Glufosinate, Glyphosate, Metazachlor, Trifluralin Ethametsulfuron, Quinmerac, Quizalofop, Clethodim, Tepraloxydim; Canola Fungicides: Azoxystrobin, Bixafen, Boscalid, Carbendazim, Cyproconazole, Difenoconazole, Dimoxystrobin, Epoxiconazole, Fluazinam, Fluopyram, Fluoxastrobin, Flusilazole, Fluxapyroxad, Iprodione, Isopyrazam, Mepiquat-chloride, Metconazole, Metominostrobin, Paclobutrazole, Penthiopyrad., Picoxystrobin, Prochloraz, Prothioconazole, Pyraclostrobin, Tebuconazole, Thiophanate-methyl, Trifloxystrobin, Vinclozolin; Canola Insecticides: Carbofuran, Thiacloprid, Deltamethrin, Imidacloprid, Clothianidin, Thiamethoxam, Acetamiprid, Dinetofuran, ß-Cyfluthrin, gamma and lambda Cyhalothrin, tau-Fluvaleriate, Ethiprole, Spinosad, Spinotoram, Flubendiamide, Rynaxypyr, Cyazypyr, 4-[[(6-Chlorpyridin-3-yl)methyl](2, 2-difluorethyl)amino]furan-2(5H)-on.

The following examples are offered by way of illustration and not by way of limitation.

EXPERIMENTAL EXAMPLES

Example 1. Discovery of Novel Pesticidal Genes from *Bacillus Thuringiensis*

Novel pesticidal genes were identified from bacterial strain ATX66600 using the following steps:
Preparation of total DNA from the strain. Total DNA contains both genomic DNA and extrachromosomal DNA. Extrachromosomal DNA contains a mixture of some or all of the following: plasmids of various size; phage chromosomes; other uncharacterized extrachromosomal molecules.
- Sequencing of the DNA. Total DNA is sequenced via Next-Generation Sequencing methods.

Identification of putative toxin genes via homology and/or other computational analyses.

When required, sequence finishing of the gene of interest by one of several PCR or cloning strategies (e.g. TAIL-PCR).

Strain ATX66600 was isolated from a soil sample collected on Santa Cruz Island in the Galapagos.

TABLE 1

Novel gene identified from strain ATX66600

| Gene name | Molecular weight (kD) | Closest homolog | Nucleotide SEQ ID NO | Amino acid SEQ ID NO |
|---|---|---|---|---|
| Axmi440 | 134.6 | 37% Axmi129, | 2 | 3 |
| Axmi440.2* | | 33% Cry7Ca1 | | 4 |
| Axmi440(trun) | | 42% ZP_04148895, | | 5 |
| Axmi440.2(trun)* | | 41% Cry7Ca1 | | 6 |

*Axmi440.2 represents a protein encoded from a downstream start site relative to Axmi440. Axmi440.2(trun) represents a protein encoded from a downstream start site relative to the toxin domain of Axmi440, which is set forth herein as Axmi440(trun).

Example 2. Assays for Pesticidal Activity

The nucleotide sequences of the invention can be tested for their ability to produce pesticidal proteins. The ability of a pesticidal protein to act as a pesticide upon a pest is often assessed in a number of ways. One way well known in the art is to perform a feeding assay. In such a feeding assay, one exposes the pest to a sample containing either compounds to be tested or control samples. Often this is performed by placing the material to be tested, or a suitable dilution of such material, onto a material that the pest will ingest, such as an artificial diet. The material to be tested may be composed of a liquid, solid, or slurry. The material to be tested may be placed upon the surface and then allowed to dry. Alternatively, the material to be tested may be mixed with a molten artificial diet, and then dispensed into the assay chamber. The assay chamber may be, for example, a cup, a dish, or a well of a microtiter plate.

Assays for sucking pests (for example aphids) may involve separating the test material from the insect by a partition, ideally a portion that can be pierced by the sucking mouth parts of the sucking insect, to allow ingestion of the test material. Often the test material is mixed with a feeding stimulant, such as sucrose, to promote ingestion of the test compound.

Other types of assays can include microinjection of the test material into the mouth, or gut of the pest, as well as development of transgenic plants, followed by test of the ability of the pest to feed upon the transgenic plant. Plant testing may involve isolation of the plant parts normally consumed, for example, small cages attached to a leaf, or isolation of entire plants in cages containing insects.

Other methods and approaches to assay pests are known in the art, and can be found, for example in Robertson and Preisler, eds. (1992) *Pesticide bioassays with arthropods*, CRC, Boca Raton, Fla. Alternatively, assays are commonly described in the journals *Arthropod Management Tests* and *Journal of Economic Entomology* or by discussion with members of the Entomological Society of America (ESA).

In some embodiments, the DNA regions encoding the toxin region of the pesticidal proteins disclosed herein are cloned into the *E. coli* expression vector pMAL-C4× behind the *malE* gene coding for Maltose binding protein (MBP). These in-frame fusions result in MBP-Axmi fusion proteins expression in *E. coli*.

For expression in *E. coli*, BL21*DE3 are transformed with individual plasmids. Single colonies are inoculated in LB supplemented with carbenicillin and glucose, and grown overnight at 37° C. The following day, fresh medium is inoculated with 1% of overnight culture and grown at 37° C. to logarithmic phase. Subsequently, cultures are induced with 0.3 mM IPTG overnight at 20° C. Each cell pellet is suspended in 20 mM Tris-Cl buffer, pH 7.4+200 mM NaCl+1 mM DTT+protease inhibitors and sonicated. Analysis by SDS-PAGE can be used to confirm expression of the fusion proteins.

Total cell free extracts are then run over amylose column attached to fast protein liquid chromatography (FPLC) for affinity purification of MBP-axmi fusion proteins. Bound fusion proteins are eluted from the resin with 10 mM maltose solution. Purified fusion proteins are then cleaved with either Factor Xa or trypsin to remove the amino terminal MBP tag from the Axmi protein. Cleavage and solubility of the proteins can be determined by SDS-PAGE Example 3. Expression and Purification A truncated variant of Axmi440 (which is set forth herein as SEQ ID NO:5) was expressed and assayed for bioactivity. The gene was PCR amplified from Strain ATX66600 using HERCULASE® II Fusion DNA Polymerase with primers incorporating an AscI linker at the 3' end. Amplified PCR product was digested with AscI and ligated into the pMa1C4× vector to create plasmid pAX8548. The clone was confirmed by sequencing and pAX8548 was transformed in B121 competent cells. A single colony was inoculated in LB media and grown at 37° C. until log phase, and induced with 0.5 mM IPTG at 20° C. for 16 hours. Purified Axmi440 was digested with Factor Xa at a 1:50 ratio at room temperature overnight. Purified Axmi440 was submitted to bioassay vs. selected insect pests according to standard protocol. The results are shown in Table 2.

TABLE 2

Stunting and Mortality Scores

| Pest Group | Stunting Score | Mortality Percentage |
|---|---|---|
| *Plutella xylostella* (DBM) | 4 | 100% |
| *Pseudoplusia includens* (SBL) | 2 | 25% |
| *Diatraea grandiosella* (SWCB) | 4 | 50% |
| *Anticarsia gemmatalis* (VBC) | 4 | 0% |

Example 4. Vectoring of Genes for Plant Expression

The coding regions of the invention are connected with appropriate promoter and terminator sequences for expression in plants. Such sequences are well known in the art and may include the rice actin promoter or maize ubiquitin promoter for expression in monocots, the *Arabidopsis* UBQ3 promoter or CaMV 35S promoter for expression in dicots, and the nos or PinII terminators. Techniques for producing and confirming promoter—gene—terminator constructs also are well known in the art.

In one aspect of the invention, synthetic DNA sequences are designed and generated. These synthetic sequences have altered nucleotide sequence relative to the parent sequence, but encode proteins that are essentially identical to the parent sequence.

In another aspect of the invention, modified versions of the synthetic genes are designed such that the resulting peptide is targeted to a plant organelle, such as the endoplasmic reticulum or the apoplast. Peptide sequences known to result in targeting of fusion proteins to plant organelles are known in the art. For example, the N-terminal region of the acid phosphatase gene from the White Lupin *Lupinus albus* (GENBANK® ID GI:14276838, Miller et al. (2001) *Plant Physiology* 127: 594-606) is known in the art to result in endoplasmic reticulum targeting of heterologous proteins. If the resulting fusion protein also contains an endoplasmic reticulum retention sequence comprising the peptide N-terminus-lysine-aspartic acid-glutamic acid-leucine (i.e., the "KDEL" motif, SEQ ID NO:7) at the C-terminus, the fusion protein will be targeted to the endoplasmic reticulum. If the fusion protein lacks an endoplasmic reticulum targeting sequence at the C-terminus, the protein will be targeted to the endoplasmic reticulum, but will ultimately be sequestered in the apoplast.

Thus, this gene encodes a fusion protein that contains the N-terminal thirty-one amino acids of the acid phosphatase gene from the White Lupin *Lupinus albus* (GENBANK® ID GI:14276838, Miller et al., 2001, supra) fused to the N-terminus of the amino acid sequence of the invention, as well as the KDEL sequence (SEQ ID NO:7) at the C-terminus. Thus, the resulting protein is predicted to be targeted the plant endoplasmic reticulum upon expression in a plant cell.

The plant expression cassettes described above are combined with an appropriate plant selectable marker to aid in the selection of transformed cells and tissues, and ligated into plant transformation vectors. These may include binary vectors from *Agrobacterium*-mediated transformation or simple plasmid vectors for aerosol or biolistic transformation.

Example 5. Transformation of Maize Cells with the Pesticidal Protein Genes Described Herein Maize ears are best collected 8-12 days after pollination. Embryos are isolated from the ears, and those embryos 0.8-1.5 mm in size are preferred for use in transformation. Embryos are plated scutellum side-up on a suitable incubation media, such as DN62A5S media (3.98 g/L N6 Salts; 1 mL/L (of 1000x Stock) N6 Vitamins; 800 mg/L L-Asparagine; 100 mg/L Myo-inositol; 1.4 g/L L-Proline; 100 mg/L Casamino acids; 50 g/L sucrose; 1 mL/L (of 1 mg/mL Stock) 2,4-D). However, media and salts other than DN62A5S are suitable and are known in the art. Embryos are incubated overnight at 25° C. in the dark. However, it is not necessary per se to incubate the embryos overnight.

The resulting explants are transferred to mesh squares (30-40 per plate), transferred onto osmotic media for about 30-45 minutes, then transferred to a beaming plate (see, for example, PCT Publication No. WO/0138514 and U.S. Pat. No. 5,240,842).

DNA constructs designed to the genes of the invention in plant cells are accelerated into plant tissue using an aerosol beam accelerator, using conditions essentially as described in PCT Publication No. WO/0138514. After beaming, embryos are incubated for about 30 min on osmotic media, and placed onto incubation media overnight at 25° C. in the dark. To avoid unduly damaging beamed explants, they are incubated for at least 24 hours prior to transfer to recovery media. Embryos are then spread onto recovery period media, for about 5 days, 25° C. in the dark, then transferred to a selection media. Explants are incubated in selection media for up to eight weeks, depending on the nature and characteristics of the particular selection utilized. After the selection period, the resulting callus is transferred to embryo maturation media, until the formation of mature somatic embryos is observed. The resulting mature somatic embryos are then placed under low light, and the process of regeneration is initiated by methods known in the art. The resulting shoots are allowed to root on rooting media, and the resulting plants are transferred to nursery pots and propagated as transgenic plants.

| Materials DN62A5S Media | | |
|---|---|---|
| Components | Per Liter | Source |
| Chu's N6 Basal Salt Mixture (Prod. No. C 416) | 3.98 g/L | Phytotechnology Labs |
| Chu's N6 Vitamin Solution (Prod. No. C 149) | 1 mL/L (of 1000x Stock) | Phytotechnology Labs |
| L-Asparagine | 800 mg/L | Phytotechnology Labs |
| Myo-inositol | 100 mg/L | Sigma |
| L-Proline | 1.4 g/L | Phytotechnology Labs |
| Casamino acids | 100 mg/L | Fisher Scientific |
| Sucrose | 50 g/L | Phytotechnology Labs |
| 2,4-D (Prod. No. D-7299) | 1 mL/L (of 1 mg/mL Stock) | Sigma |

The pH of the solution is adjusted to pH 5.8 with 1N KOH/1N KCl Gelrite (Sigma) is added at a concentration up to 3 g/L, and the media is autoclaved. After cooling to 50° C., 2 ml/L of a 5 mg/ml stock solution of silver nitrate (Phytotechnology Labs) is added.

Example 6. Transformation of Genes of the Invention in Plant Cells by *Agrobacterium*-Mediated Transformation Ears are best collected 8-12 days after pollination. Embryos are isolated from the ears, and those embryos 0.8-1.5 mm in size are preferred for use in transformation. Embryos are plated scutellum side-up on a suitable incubation media, and incubated overnight at 25° C. in the dark. However, it is not necessary per se to incubate the embryos overnight. Embryos are contacted with an *Agrobacterium* strain containing the appropriate vectors for Ti plasmid mediated transfer for about 5-10 min, and then plated onto co-cultivation media for about 3 days (25° C. in the dark). After co-cultivation, explants are transferred to recovery period media for about five days (at 25° C. in the dark). Explants are incubated in selection media for up to eight weeks, depending on the nature and characteristics of the particular selection utilized. After the selection period, the resulting callus is transferred to embryo maturation media, until the formation of mature somatic embryos is observed. The resulting mature somatic embryos are then placed under low light, and the process of regeneration is initiated as known in the art.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

That which is claimed:

1. A construct comprising a heterologous promoter operably linked to a nucleotide sequence encoding an amino acid sequence having pesticidal activity, wherein said nucleotide sequence is selected from the group consisting of:
   a) the nucleotide sequence set forth in SEQ ID NO:2, wherein the GTG at positions 1-3 of SEQ ID NO:2 is changed to ATG;
   b) a nucleotide sequence that encodes a polypeptide comprising the amino acid sequence of any of SEQ ID NO:3-6;
   c) a nucleotide sequence that encodes a polypeptide comprising an amino acid sequence having at least 95% sequence identity to the amino acid sequence of any of SEQ ID NO:3-6.

2. The construct of claim 1, wherein said nucleotide sequence has been optimized for expression in a plant.

3. The construct of claim 1, wherein said promoter is capable of directing expression of said nucleotide sequence in a plant cell.

4. A vector comprising the construct of claim 1.

5. The vector of claim 4, further comprising a nucleic acid molecule encoding a heterologous polypeptide.

6. A host cell that contains the construct of claim 1.

7. The host cell of claim 6 that is a bacterial host cell.

8. The host cell of claim 6 that is a plant cell.

9. A transgenic plant comprising the host cell of claim 8.

10. The transgenic plant of claim 9, wherein said plant is selected from the group consisting of maize, sorghum, wheat, cabbage, sunflower, tomato, crucifers, peppers, potato, cotton, rice, soybean, sugarbeet, sugarcane, tobacco, barley, and oilseed rape.

11. A transgenic seed comprising the construct of claim 1.

12. A recombinant polypeptide with pesticidal activity, wherein said polypeptide comprises a heterologous leader sequence or a transit peptide operably linked to a polypeptide selected from the group consisting of:
   a) a polypeptide comprising the amino acid sequence of any of SEQ ID NO:3-6; and b) a polypeptide comprising an amino acid sequence having at least 95% sequence identity to the amino acid sequence of any of SEQ ID NO:3-6.

13. A composition comprising the polypeptide of claim 12.

14. The composition of claim 13, wherein said composition is selected from the group consisting of a powder, dust, pellet, granule, spray, emulsion, colloid, and solution.

15. The composition of claim 13, wherein said composition is prepared by desiccation, lyophilization, homogenization, extraction, filtration, centrifugation, sedimentation, or concentration of a culture of bacterial cells.

16. The composition of claim 13, comprising from about 1% to about 99% by weight of said polypeptide.

17. A plant or plant cell having stably incorporated into its genome a DNA construct comprising a nucleotide sequence that encodes a protein having pesticidal activity, wherein said nucleotide sequence is selected from the group consisting of:
   a) the nucleotide sequence set forth in SEQ ID NO:2, wherein the GTG at positions 1-3 of SEQ ID NO:2 is changed to ATG;
   b) a nucleotide sequence that encodes a polypeptide comprising the amino acid sequence of any of SEQ ID NO:3-6; and
   c) a nucleotide sequence that encodes a polypeptide comprising an amino acid sequence having at least 95% sequence identity to the amino acid sequence of any of SEQ ID NO:3-6.

18. A method for increasing yield in a plant comprising growing in a field a plant or a seed thereof having stably incorporated into its genome a DNA construct comprising a nucleotide sequence that encodes a protein having pesticidal activity, wherein said nucleotide sequence is selected from the group consisting of:
   a) the nucleotide sequence set forth in SEQ ID NO:2, wherein the GTG at positions 1-3 of SEO ID NO:2 is changed to ATG;
   b) a nucleotide sequence that encodes a protein comprising the amino acid sequence of any of SEQ ID NO:3-6; and
   c) a nucleotide sequence that encodes a protein comprising an amino acid sequence having at least 95% sequence identity to the amino acid sequence of any of SEQ ID NO:3-6;
wherein said field is infested with a pest against which said protein having pesticidal activity has pesticidal activity.

* * * * *

SEQUENCE LISTING

```
<160> NUMBER OF SEQ ID NOS: 7

<210> SEQ ID NO 1
<211> LENGTH: 4299
<212> TYPE: DNA
<213> ORGANISM: Bacillus thuringiensis

<400> SEQUENCE: 1
atgaaaaaag ataatgaaat aagcaattac gttaatgata accatgtgaa ttcccataag      60
aaagttcctt tttgttgtgt catagcaatt ccagatggat ttgaactcgt accacattgt     120
tatccaaaag taatatacag tcttgagtgt ctagccctat gtaaagatgt atgtcgcaaa     180
accgtgccag tagaagggtg tggtcaggca gaaattgatt tacatgttct aaagataaag     240
ggatgcattc cttatatagt caatattgaa gtacgaccta catgtgattg gaaaggatgt     300
tcaacagact cacattcaaa agaaatcaca ttatgttgta aagagagtgt atgtattgat     360
gcagttttac aatgtagtgt gcactgtgta gacagcatag atttaaactg tgaaaatgta     420
aaggtatgtg acttaagcat acaaatttct gattgtatga attcctgtca tcttgctaaa     480
atctccggtt actttcagtt ttgctagaat aaaaataaaga taatttagag ttataagtct     540
aacaataaat gaatattata aaatgtctta aggaacaatg ttccttgtag atactttaaa     600
aaataagaag ggacgattaa ataccagaat atggaggggg gagaggggct tttcgtactg     660
atattaaaga atgaatttat atatataagt acaagtggaa aatcattgat aatgcgagta     720
tatccttgaa atgtataaat aggaggtata gatgtgaaga taaatgatgt aaatgaatgg     780
gataatgtag cagaggtgac tgaaaaccct cttgcaccta gcattccgta caatgttcta     840
caacgtaaag aaaacacagc aaacgaatta acctatgata attataattt ccaagatttt     900
ttaacattag gttatgaaga tattactcaa gcagctaatg cgcaagatgt aattaatacg     960
acactaaatg taactgcaac aattttgaat ttcttaggag tcccgtatgc agggactgta    1020
atttctatgt atcaaaaact atttaattat ttatggcctt atgaagacac ttcagaatgg    1080 gataaaaatga tggcggcagt agaagcgcta ataaatcaaa aatcaatgga gacagttaaa    1140
agtttggctc ttgcggattt agatggttta gggcgcaact taaagtctta tggaaatgca    1200
cttaagaatt ggaatgagaa taaaaatgat gcagatagca cagctttagt gttagatcgc    1260
tttagaacag ttaatgaact atttgtaaat gatatggctt cttttgctcc taaaggttac    1320
gaggtactac ttctggacgt atatgcaaaa gcagcaaatc tacatttgct ttttttaaga    1380
gatgcagaac tatatggtgc agattgggga atgcctgaag atgagataaa tttattttat    1440
caagaacaag aagattatag aaaagaatat tcggaccatt gcatatcttg gtatcaaaaa    1500
gggttaaatc agtttaataa gtctagtgca ctggattgga taaaatataa tcgttacaga    1560
acccaaatga caattaatgt gttggatttt gttgcgttat atccaaatta tgatgttcgt    1620
aaatatccaa tgtccacaca cacggagctt acaagaactg tatattcaga tcctattggt    1680
tttgatgaac gaacgggaac tggtactagt ggggttcgtg cttggtatga agctggacgc    1740
tcttttgctg agatagaaaa taatgctatt cctgcacctg atatcgttaa atttataaat    1800
aaactaacag tatattcaaa aaggataaat gccagtccat tcatggccac tcgttgggca    1860
```

```
gggcattcca taactcagga cactacattt acaggttcag cacaagaaat aaagtatgga      1920
gatgtttcag gtgtccctac cacatttta tttaaaaaca cagatatta tcgtacgata       1980 tcaacggtag gaacgtatta ttatactaat ggcccttata aactgccact ttcaaaagtt    2040 cattttatg gaataaatac ttctaatcga aaggaaactt tcaattatga tcaagatatt     2100
aattttaaat ttcagcatca aaaagactca agtaatgaga tagctgtagt ccttccagga    2160
cccacagact atggggacta taataaatat agtcatcggt taagttatat ttctgatgcc   2220
cctataaaac agttcactgg gttaagctca aatgaaggtt ttgtccctgt atttggttgg    2280
atgcattcaa gcacaactcg taaaaatttt cttagtgcca atcaaatcac gcaaattcca    2340
gctgtaaagt ctcacgaata taactcatcc atggcaattg taagctcaaa cggatattgt    2400
ggcggatata ttatgaaggt ttcaaaagta tttccattca atgaagtgac agctggaaac    2460
tatgtagtag attgtgaaga ttatagtcaa caatttcgtt ttcgggttag atatgcttcc    2520
actgtaagct gtccactacg gtttgctaca ttcagcatat ctggtccaac cgttaattta    2580
gaaaaaacac tacaaaaagg tgatgaaata aaatatagtt cctttaaata ttctgaatac    2640
tcagatcctg tgaggtttaa ccctcctggt acctcaggat tccctagttt taatcttata    2700
tttgtaggat tatctgctaa tgaaaatgta tatatagata aaattgaatg tattccagtc    2760
acaaaagatg atttagacaa ggaaacatta gaaaaagcag aaaaagcggt gaatgctttg    2820
tttattgatg gtacccagaa tttaaaaaca gaagtgacag attattgtat agatcaggtt    2880
tctatgataa tagattgtgt gtctgaagaa ctatatccaa atgaaaaacg agatcttttg    2940
tatttagtaa agcatgcgaa aagacaaagt aatacacgaa acttaattct ggattccaac    3000
tttacttcta ttaattcaga agatgttaac ggttggtatg aagtcctgg tcttatagta    3060 gaatctggag atgtggtctt taagaaaaat tatgtacatt tacgtggtcc aaatgatgaa    3120
cgctatccaa cgtacctgta tcaaaaaata gacgaatcaa aattaacaga atatacaaga    3180
tatcaattgc gaggtttcat agaaggaagt cgtggtttgg aagtatatgt aattcgttat    3240
gatgcaaaac atgaaacact gaatgtttta ggggatttat ctctagataa tctgtcttac    3300
aacgaatgtg gtcaaccaga tcgctgttca caagaaccat atattgaaca gaggttacaa    3360
caagaagaag ttgctaatga acgtgcatgt cattttgatt ccaatgactc cctgtcttca    3420
tcaaatggat atccttctga ttcacatcat ttatccctac acgttgatac cggatctatt    3480
gattttaaag aaaatttagg tatctggatt ttattcaaat tatcgacaac agatggatat    3540
gcaaagattg ggaatattga attggtggaa gagggaccat taacaggaag tgcgctcgga    3600
tctataaaaa gaatggaaaa taaatggaaa gaaaaagtgg agagcattcg tttacaaggg    3660
aaaaaagcat atgatacagc aaaactatat attgataatc tatttgaagg ctctcaaaat    3720
acaaagttgt atccttttgt cacattttta acactatcca atgctcgaca acttataaat    3780
aagatttata acaaatatag tccttggtta tcattaattc ctggagtgaa ttatgattta    3840
tttgaagaat tagccgtcag atttcaaaat gctttacaat tatatgatac aagaaacttg    3900
atacaaaatg ggcgattat tgacggttta gtgagttgga tgacaacacc aggtgtacaa    3960
gtgcgaaaag atagtgcatc ctccatactt gagttaaata gttgggaaga acaagtggta    4020
caaaaagtac cagtgtgcca agggtatggg tatgtattac gtgtaacagc aagtaaagaa    4080
gatttaggag agggatatat taaggttagt gatgaaatgg gtaatagtga tactataata    4140
tttagtgcat gtaataattc aaataatgac gtctctataa ataattatgt tacacaagag    4200
ttagagttct tccctgattc agattacgtt caccttgaaa ttggggaaac agaaggaaca    4260
```

```
tttcagattg taagtgttga gctaatttta atggaagat                       4299

<210> SEQ ID NO 2
<211> LENGTH: 3546
<212> TYPE: DNA
<213> ORGANISM: Bacillus thuringiensis

<400> SEQUENCE: 2
gtgaagataa atgatgtaaa tgaatgggat aatgtagcag aggtgactga aaaccctctt   60
gcacctagca ttccgtacaa tgttctacaa cgtaaagaaa acacagcaaa cgaattaacc  120
tatgataatt ataatttcca agatttttta acattaggtt atgaagatat tactcaagca  180
gctaatgcgc aagatgtaat taatacgaca ctaaatgtaa ctgcaacaat tttgaatttc  240
ttaggagtcc cgtatgcagg gactgtaatt tctatgtatc aaaaactatt taattattta  300
tggccttatg aagacacttc agaatgggat aaaatgatgg cggcagtaga agcgctaata  360
aatcaaaaaa tcaatgagac agttaaaagt ttggctcttg cggatttaga tggtttaggg  420
cgcaacttaa agtcttatgg aaatgcactt aagaattgga atgagaataa aaatgatgca  480
gatagcacag ctttagtgtt agatcgcttt agaacagtta atgaactatt tgtaaatgat  540
atggcttctt ttgctcctaa aggttacgag gtactacttc tggacgtata tgcaaaagca  600
gcaaatctac atttgctttt tttaagagat gcagaactat atggtgcaga ttggggaatg  660
cctgaagatg agataaattt attttatcaa gaacaagaag attatagaaa agaatattcg  720
gaccattgca tatcttggta tcaaaaaggg ttaaatcagt ttaataagtc tagtgcactg  780
gattggataa aatataatcg ttacagaacc caaatgacaa ttaatgtgtt ggattttgtt  840
gcgttatatc caaattatga tgttcgtaaa tatccaatgt ccacacacac ggagcttaca  900
agaactgtat attcagatcc tattggtttt gatgaacgaa cgggaactgg tactagtggg  960
gttcgtgctt ggtatgaagc tggacgctct tttgctgaga tagaaaataa tgctattcct 1020
gcacctgata tcgttaaatt tataaataaa ctaacagtat attcaaaaag gataaatgcc 1080
agtccattca tggccactcg ttgggcaggg cattccataa ctcaggacac tacatttaca 1140
ggttcagcac aagaaataaa gtatggagat gtttcaggtg tccctaccac atttttattt 1200
aaaaacacag atatttatcg tacgatatca acggtaggaa cgtattatta tactaatggc 1260
ccttataaac tgccactttc aaaagttcat ttttatggaa taaatacttc taatcgaaag 1320
gaaactttca attatgatca agatattaat tttaaatttc agcatcaaaa agactcaagt 1380
aatgagatag ctgtagtcct tccaggaccc acagactatg ggactataa taaatatagt 1440 catcggttaa gttatatttc tgatgcccct ataaaacagt tcactgggtt aagctcaaat 1500
gaaggttttg tccctgtatt tggttggatg cattcaagca caactcgtaa aaattttctt 1560
agtgccaatc aaatcacgca aattccagct gtaaagtctc acgaatataa ctcatccatg 1620
gcaattgtaa gctcaaacgg atattgtggc ggatatatta tgaaggtttc aaaagtattt 1680
ccattcaatg aagtgacagc tggaaactat gtagtagatt gtgaagatta tagtcaacaa 1740
tttcgttttc gggttagata tgcttccact gtaagctgtc cactacggtt tgctacattc 1800
agcatatctg gtccaaccgt taatttagaa aaacactac aaaaaggtga tgaaataaaa 1860
tatagttcct ttaaatattc tgaatactca gatcctgtga ggtttaaccc tcctggtacc 1920
tcaggattcc ctagttttaa tcttatattt gtaggattat ctgctaatga aaatgtatat 1980
atagataaaa ttgaatgtat tccagtcaca aaagatgatt tagacaagga aacattagaa 2040
```

-continued

```
aaagcagaaa aagcggtgaa tgctttgttt attgatggta cccagaattt aaaaacagaa    2100
gtgacagatt attgtataga tcaggtttct atgataatag attgtgtgtc tgaagaacta    2160
tatccaaatg aaaaacgaga tcttttgtat ttagtaaagc atgcgaaaag acaaagtaat    2220
acacgaaact taattctgga ttccaacttt acttctatta attcagaaga tgttaacggt    2280
tggtatggaa gtcctggtct tatagtagaa tctggagatg tggtctttaa agaaaattat    2340
gtacatttac gtggtccaaa tgatgaacgc tatccaacgt acctgtatca aaaaatagac    2400
gaatcaaaat taacagaata tacaagatat caattgcgag gtttcataga aggaagtcgt    2460
ggtttggaag tatatgtaat tcgttatgat gcaaaacatg aaacactgaa tgttttaggg    2520
gatttatctc tagataatct gtcttacaac gaatgtggtc aaccagatcg ctgttcacaa    2580
gaaccatata ttgaacagag gttacaacaa gaagaagttg ctaatgaacg tgcatgtcat    2640
tttgattcca atgactccct gtcttcatca aatggatatc cttctgattc acatcattta    2700
tccctacacg ttgataccgg atctattgat tttaaagaaa atttaggtat ctggattta     2760
ttcaaattat cgacaacaga tggatatgca agattggga atattgaatt ggtggaagag     2820
ggaccattaa caggaagtgc gctcggatct ataaaaagaa tggaaaataa atggaaagaa    2880
aaagtggaga gcattcgttt acaagggaaa aaagcatatg tacagcaaa actatatatt     2940
gataatctat ttgaaggctc tcaaaataca aagttgtatc ctttttgtcac atttttaaca    3000
ctatccaatg ctcgacaact tataaataag atttataaca aatatagtcc ttggttatca    3060
ttaattcctg gagtgaatta tgatttattt gaagaattag ccgtcagatt tcaaaatgct    3120
ttacaattat atgatacaag aaacttgata caaaatgggc gatttattga cggtttagtg    3180
agttggatga caacaccagg tgtacaagtg cgaaaagata gtgcatcctc catacttgag    3240
ttaaatagtt gggaagaaca agtggtacaa aaagtaccag tgtgccaagg gtatgggtat    3300
gtattacgtg taacagcaag taaagaagat ttaggagagg gatatattaa ggttagtgat    3360
gaaatgggta atagtgatac tataatattt agtgcatgta ataattcaaa taatgacgtc    3420
tctataaata attatgttac acaagagtta gagttcttcc ctgattcaga ttacgttcac    3480
cttgaaattg gggaaacaga aggaacattt cagattgtaa gtgttgagct aatttaatg     3540
gaagat                                                              3546
```

<210> SEQ ID NO 3
<211> LENGTH: 1182
<212> TYPE: PRT
<213> ORGANISM: Bacillus thuringiensis

<400> SEQUENCE: 3

```
Met Lys Ile Asn Asp Val Asn Glu Trp Asp Asn Val Ala Glu Val Thr
1               5                   10                  15

Glu Asn Pro Leu Ala Pro Ser Ile Pro Tyr Asn Val Leu Gln Arg Lys
            20                  25                  30

Glu Asn Thr Ala Asn Glu Leu Thr Tyr Asp Asn Tyr Asn Phe Gln Asp
        35                  40                  45

Phe Leu Thr Leu Gly Tyr Glu Asp Ile Thr Gln Ala Ala Asn Ala Gln
    50                  55                  60

Asp Val Ile Asn Thr Thr Leu Asn Val Thr Ala Thr Ile Leu Asn Phe
65                  70                  75                  80

Leu Gly Val Pro Tyr Ala Gly Thr Val Ile Ser Met Tyr Gln Lys Leu
                85                  90                  95

Phe Asn Tyr Leu Trp Pro Tyr Glu Asp Thr Ser Glu Trp Asp Lys Met
```

-continued

```
            100                 105                 110
Met Ala Ala Val Glu Ala Leu Ile Asn Gln Lys Ile Asn Glu Thr Val
            115                 120                 125
Lys Ser Leu Ala Leu Ala Asp Leu Asp Gly Leu Gly Arg Asn Leu Lys
            130                 135             140
Ser Tyr Gly Asn Ala Leu Lys Asn Trp Asn Glu Asn Lys Asn Asp Ala
145                     150                 155                 160
Asp Ser Thr Ala Leu Val Leu Asp Arg Phe Arg Thr Val Asn Glu Leu
                    165                 170                 175
Phe Val Asn Asp Met Ala Ser Phe Ala Pro Lys Gly Tyr Glu Val Leu
                180                 185                 190
Leu Leu Asp Val Tyr Ala Lys Ala Asn Leu His Leu Leu Phe Leu
            195                 200                 205
Arg Asp Ala Glu Leu Tyr Gly Ala Asp Trp Gly Met Pro Glu Asp Glu
            210                 215                 220
Ile Asn Leu Phe Tyr Gln Glu Gln Asp Tyr Arg Lys Glu Tyr Ser
225                 230                 235                 240
Asp His Cys Ile Ser Trp Tyr Gln Lys Gly Leu Asn Gln Phe Asn Lys
                    245                 250                 255
Ser Ser Ala Leu Asp Trp Ile Lys Tyr Asn Arg Tyr Arg Thr Gln Met
                260                 265                 270
Thr Ile Asn Val Leu Asp Phe Val Ala Leu Tyr Pro Asn Tyr Asp Val
            275                 280                 285
Arg Lys Tyr Pro Met Ser Thr His Thr Glu Leu Thr Arg Thr Val Tyr
            290                 295                 300
Ser Asp Pro Ile Gly Phe Asp Glu Arg Thr Gly Thr Gly Thr Ser Gly
305                 310                 315                 320
Val Arg Ala Trp Tyr Glu Ala Gly Arg Ser Phe Ala Glu Ile Glu Asn
                    325                 330                 335
Asn Ala Ile Pro Ala Pro Asp Ile Val Lys Phe Ile Asn Lys Leu Thr
                340                 345                 350
Val Tyr Ser Lys Arg Ile Asn Ala Ser Pro Phe Met Ala Thr Arg Trp
            355                 360                 365
Ala Gly His Ser Ile Thr Gln Asp Thr Thr Phe Thr Gly Ser Ala Gln
            370                 375             380
Glu Ile Lys Tyr Gly Asp Val Ser Gly Val Pro Thr Thr Phe Leu Phe
385                 390                 395                 400
Lys Asn Thr Asp Ile Tyr Arg Thr Ile Ser Thr Val Gly Thr Tyr Tyr
                    405                 410                 415
Tyr Thr Asn Gly Pro Tyr Lys Leu Pro Leu Ser Lys Val His Phe Tyr
                420                 425                 430
Gly Ile Asn Thr Ser Asn Arg Lys Glu Thr Phe Asn Tyr Asp Gln Asp
            435                 440                 445
Ile Asn Phe Lys Phe Gln His Gln Lys Asp Ser Asn Glu Ile Ala
            450                 455                 460
Val Val Leu Pro Gly Pro Thr Asp Tyr Gly Asp Tyr Asn Lys Tyr Ser
465                 470                 475                 480
His Arg Leu Ser Tyr Ile Ser Asp Ala Pro Ile Lys Gln Phe Thr Gly
                    485                 490                 495
Leu Ser Ser Asn Glu Gly Phe Val Pro Val Phe Gly Trp Met His Ser
                500                 505                 510
Ser Thr Thr Arg Lys Asn Phe Leu Ser Ala Asn Gln Ile Thr Gln Ile
            515                 520                 525
```

```
Pro Ala Val Lys Ser His Glu Tyr Asn Ser Ser Met Ala Ile Val Ser
    530                 535                 540

Ser Asn Gly Tyr Cys Gly Gly Tyr Ile Met Lys Val Ser Lys Val Phe
545                 550                 555                 560

Pro Phe Asn Glu Val Thr Ala Gly Asn Tyr Val Val Asp Cys Glu Asp
                565                 570                 575

Tyr Ser Gln Gln Phe Arg Phe Arg Val Arg Tyr Ala Ser Thr Val Ser
            580                 585                 590

Cys Pro Leu Arg Phe Ala Thr Phe Ser Ile Ser Gly Pro Thr Val Asn
        595                 600                 605

Leu Glu Lys Thr Leu Gln Lys Gly Asp Glu Ile Lys Tyr Ser Ser Phe
    610                 615                 620

Lys Tyr Ser Glu Tyr Ser Asp Pro Val Arg Phe Asn Pro Pro Gly Thr
625                 630                 635                 640

Ser Gly Phe Pro Ser Phe Asn Leu Ile Phe Val Gly Leu Ser Ala Asn
                645                 650                 655

Glu Asn Val Tyr Ile Asp Lys Ile Glu Cys Ile Pro Val Thr Lys Asp
            660                 665                 670

Asp Leu Asp Lys Glu Thr Leu Glu Lys Ala Glu Lys Ala Val Asn Ala
        675                 680                 685

Leu Phe Ile Asp Gly Thr Gln Asn Leu Lys Thr Glu Val Thr Asp Tyr
    690                 695                 700

Cys Ile Asp Gln Val Ser Met Ile Ile Asp Cys Val Ser Glu Glu Leu
705                 710                 715                 720

Tyr Pro Asn Glu Lys Arg Asp Leu Leu Tyr Leu Val Lys His Ala Lys
                725                 730                 735

Arg Gln Ser Asn Thr Arg Asn Leu Ile Leu Asp Ser Asn Phe Thr Ser
            740                 745                 750

Ile Asn Ser Glu Asp Val Asn Gly Trp Tyr Gly Ser Pro Gly Leu Ile
        755                 760                 765

Val Glu Ser Gly Asp Val Val Phe Lys Glu Asn Tyr Val His Leu Arg
    770                 775                 780

Gly Pro Asn Asp Glu Arg Tyr Pro Thr Tyr Leu Tyr Gln Lys Ile Asp
785                 790                 795                 800

Glu Ser Lys Leu Thr Glu Tyr Thr Arg Tyr Gln Leu Arg Gly Phe Ile
                805                 810                 815

Glu Gly Ser Arg Gly Leu Glu Val Tyr Val Ile Arg Tyr Asp Ala Lys
            820                 825                 830

His Glu Thr Leu Asn Val Leu Gly Asp Leu Ser Leu Asp Asn Leu Ser
        835                 840                 845

Tyr Asn Glu Cys Gly Gln Pro Asp Arg Cys Ser Gln Glu Pro Tyr Ile
    850                 855                 860

Glu Gln Arg Leu Gln Gln Glu Val Ala Asn Glu Arg Ala Cys His
865                 870                 875                 880

Phe Asp Ser Asn Asp Ser Leu Ser Ser Asn Gly Tyr Pro Ser Asp
                885                 890                 895

Ser His His Leu Ser Leu His Val Asp Thr Gly Ser Ile Asp Phe Lys
            900                 905                 910

Glu Asn Leu Gly Ile Trp Ile Leu Phe Lys Leu Ser Thr Thr Asp Gly
        915                 920                 925

Tyr Ala Lys Ile Gly Asn Ile Glu Leu Val Glu Glu Gly Pro Leu Thr
    930                 935                 940
```

```
Gly Ser Ala Leu Gly Ser Ile Lys Arg Met Glu Asn Lys Trp Lys Glu
945                 950                 955                 960

Lys Val Glu Ser Ile Arg Leu Gln Gly Lys Lys Ala Tyr Asp Thr Ala
                965                 970                 975

Lys Leu Tyr Ile Asp Asn Leu Phe Glu Gly Ser Gln Asn Thr Lys Leu
            980                 985                 990

Tyr Pro Phe Val Thr Phe Leu Thr Leu Ser Asn Ala Arg Gln Leu Ile
        995                 1000                1005

Asn Lys Ile Tyr Asn Lys Tyr Ser Pro Trp Leu Ser Leu Ile Pro
    1010                1015                1020

Gly Val Asn Tyr Asp Leu Phe Glu Glu Leu Ala Val Arg Phe Gln
    1025                1030                1035

Asn Ala Leu Gln Leu Tyr Asp Thr Arg Asn Leu Ile Gln Asn Gly
    1040                1045                1050

Arg Phe Ile Asp Gly Leu Val Ser Trp Met Thr Thr Pro Gly Val
    1055                1060                1065

Gln Val Arg Lys Asp Ser Ala Ser Ser Ile Leu Glu Leu Asn Ser
    1070                1075                1080

Trp Glu Glu Gln Val Val Gln Lys Val Pro Val Cys Gln Gly Tyr
    1085                1090                1095

Gly Tyr Val Leu Arg Val Thr Ala Ser Lys Glu Asp Leu Gly Glu
    1100                1105                1110

Gly Tyr Ile Lys Val Ser Asp Glu Met Gly Asn Ser Asp Thr Ile
    1115                1120                1125

Ile Phe Ser Ala Cys Asn Asn Ser Asn Asn Asp Val Ser Ile Asn
    1130                1135                1140

Asn Tyr Val Thr Gln Glu Leu Glu Phe Phe Pro Asp Ser Asp Tyr
    1145                1150                1155

Val His Leu Glu Ile Gly Glu Thr Glu Gly Thr Phe Gln Ile Val
    1160                1165                1170

Ser Val Glu Leu Ile Leu Met Glu Asp
    1175                1180

<210> SEQ ID NO 4
<211> LENGTH: 1091
<212> TYPE: PRT
<213> ORGANISM: Bacillus thuringiensis

<400> SEQUENCE: 4

Met Tyr Gln Lys Leu Phe Asn Tyr Leu Trp Pro Tyr Glu Asp Thr Ser
1               5                   10                  15

Glu Trp Asp Lys Met Met Ala Ala Val Glu Ala Leu Ile Asn Gln Lys
                20                  25                  30

Ile Asn Glu Thr Val Lys Ser Leu Ala Leu Ala Asp Leu Asp Gly Leu
            35                  40                  45

Gly Arg Asn Leu Lys Ser Tyr Gly Asn Ala Leu Lys Asn Trp Asn Glu
        50                  55                  60

Asn Lys Asn Asp Ala Asp Ser Thr Ala Leu Val Leu Asp Arg Phe Arg
65                  70                  75                  80

Thr Val Asn Glu Leu Phe Val Asn Asp Met Ala Ser Phe Ala Pro Lys
                85                  90                  95

Gly Tyr Glu Val Leu Leu Leu Asp Val Tyr Ala Lys Ala Ala Asn Leu
            100                 105                 110

His Leu Leu Phe Leu Arg Asp Ala Glu Leu Tyr Gly Ala Asp Trp Gly
        115                 120                 125
```

```
Met Pro Glu Asp Glu Ile Asn Leu Phe Tyr Gln Glu Gln Asp Tyr
    130                 135                 140

Arg Lys Glu Tyr Ser Asp His Cys Ile Ser Trp Tyr Gln Lys Gly Leu
145                 150                 155                 160

Asn Gln Phe Asn Lys Ser Ser Ala Leu Asp Trp Ile Lys Tyr Asn Arg
                165                 170                 175

Tyr Arg Thr Gln Met Thr Ile Asn Val Leu Asp Phe Val Ala Leu Tyr
                180                 185                 190

Pro Asn Tyr Asp Val Arg Lys Tyr Pro Met Ser Thr His Thr Glu Leu
            195                 200                 205

Thr Arg Thr Val Tyr Ser Asp Pro Ile Gly Phe Asp Glu Arg Thr Gly
    210                 215                 220

Thr Gly Thr Ser Gly Val Arg Ala Trp Tyr Glu Ala Gly Arg Ser Phe
225                 230                 235                 240

Ala Glu Ile Glu Asn Asn Ala Ile Pro Ala Pro Asp Ile Val Lys Phe
                245                 250                 255

Ile Asn Lys Leu Thr Val Tyr Ser Lys Arg Ile Asn Ala Ser Pro Phe
                260                 265                 270

Met Ala Thr Arg Trp Ala Gly His Ser Ile Thr Gln Asp Thr Thr Phe
            275                 280                 285

Thr Gly Ser Ala Gln Glu Ile Lys Tyr Gly Asp Val Ser Gly Val Pro
    290                 295                 300

Thr Thr Phe Leu Phe Lys Asn Thr Asp Ile Tyr Arg Thr Ile Ser Thr
305                 310                 315                 320

Val Gly Thr Tyr Tyr Tyr Thr Asn Gly Pro Tyr Lys Leu Pro Leu Ser
                325                 330                 335

Lys Val His Phe Tyr Gly Ile Asn Thr Ser Asn Arg Lys Glu Thr Phe
                340                 345                 350

Asn Tyr Asp Gln Asp Ile Asn Phe Lys Phe Gln His Gln Lys Asp Ser
            355                 360                 365

Ser Asn Glu Ile Ala Val Val Leu Pro Gly Pro Thr Asp Tyr Gly Asp
    370                 375                 380

Tyr Asn Lys Tyr Ser His Arg Leu Ser Tyr Ile Ser Asp Ala Pro Ile
385                 390                 395                 400

Lys Gln Phe Thr Gly Leu Ser Ser Asn Glu Gly Phe Val Pro Val Phe
                405                 410                 415

Gly Trp Met His Ser Ser Thr Thr Arg Lys Asn Phe Leu Ser Ala Asn
            420                 425                 430

Gln Ile Thr Gln Ile Pro Ala Val Lys Ser His Glu Tyr Asn Ser Ser
    435                 440                 445

Met Ala Ile Val Ser Ser Asn Gly Tyr Cys Gly Gly Tyr Ile Met Lys
    450                 455                 460

Val Ser Lys Val Phe Pro Phe Asn Glu Val Thr Ala Gly Asn Tyr Val
465                 470                 475                 480

Val Asp Cys Glu Asp Tyr Ser Gln Gln Phe Arg Phe Arg Val Arg Tyr
                485                 490                 495

Ala Ser Thr Val Ser Cys Pro Leu Arg Phe Ala Thr Phe Ser Ile Ser
                500                 505                 510

Gly Pro Thr Val Asn Leu Glu Lys Thr Leu Gln Lys Gly Asp Glu Ile
    515                 520                 525

Lys Tyr Ser Ser Phe Lys Tyr Ser Glu Tyr Ser Asp Pro Val Arg Phe
    530                 535                 540
```

-continued

```
Asn Pro Pro Gly Thr Ser Gly Phe Pro Ser Phe Asn Leu Ile Phe Val
545                 550                 555                 560

Gly Leu Ser Ala Asn Glu Asn Val Tyr Ile Asp Lys Ile Glu Cys Ile
            565                 570                 575

Pro Val Thr Lys Asp Asp Leu Asp Lys Glu Thr Leu Glu Lys Ala Glu
                580                 585                 590

Lys Ala Val Asn Ala Leu Phe Ile Asp Gly Thr Gln Asn Leu Lys Thr
            595                 600                 605

Glu Val Thr Asp Tyr Cys Ile Asp Gln Val Ser Met Ile Ile Asp Cys
    610                 615                 620

Val Ser Glu Glu Leu Tyr Pro Asn Glu Lys Arg Asp Leu Leu Tyr Leu
625                 630                 635                 640

Val Lys His Ala Lys Arg Gln Ser Asn Thr Arg Asn Leu Ile Leu Asp
            645                 650                 655

Ser Asn Phe Thr Ser Ile Asn Ser Glu Asp Val Asn Gly Trp Tyr Gly
                660                 665                 670

Ser Pro Gly Leu Ile Val Glu Ser Gly Asp Val Val Phe Lys Glu Asn
            675                 680                 685

Tyr Val His Leu Arg Gly Pro Asn Asp Glu Arg Tyr Pro Thr Tyr Leu
690                 695                 700

Tyr Gln Lys Ile Asp Glu Ser Lys Leu Thr Glu Tyr Thr Arg Tyr Gln
705                 710                 715                 720

Leu Arg Gly Phe Ile Glu Gly Ser Arg Gly Leu Glu Val Tyr Val Ile
                725                 730                 735

Arg Tyr Asp Ala Lys His Glu Thr Leu Asn Val Leu Gly Asp Leu Ser
            740                 745                 750

Leu Asp Asn Leu Ser Tyr Asn Glu Cys Gly Gln Pro Asp Arg Cys Ser
            755                 760                 765

Gln Glu Pro Tyr Ile Glu Gln Arg Leu Gln Glu Glu Val Ala Asn
    770                 775                 780

Glu Arg Ala Cys His Phe Asp Ser Asn Asp Ser Leu Ser Ser Ser Asn
785                 790                 795                 800

Gly Tyr Pro Ser Asp Ser His His Leu Ser Leu His Val Asp Thr Gly
                805                 810                 815

Ser Ile Asp Phe Lys Glu Asn Leu Gly Ile Trp Ile Leu Phe Lys Leu
            820                 825                 830

Ser Thr Thr Asp Gly Tyr Ala Lys Ile Gly Asn Ile Glu Leu Val Glu
            835                 840                 845

Glu Gly Pro Leu Thr Gly Ser Ala Leu Gly Ser Ile Lys Arg Met Glu
850                 855                 860

Asn Lys Trp Lys Glu Lys Val Glu Ser Ile Arg Leu Gln Gly Lys Lys
865                 870                 875                 880

Ala Tyr Asp Thr Ala Lys Leu Tyr Ile Asp Asn Leu Phe Glu Gly Ser
                885                 890                 895

Gln Asn Thr Lys Leu Tyr Pro Phe Val Thr Phe Leu Thr Leu Ser Asn
            900                 905                 910

Ala Arg Gln Leu Ile Asn Lys Ile Tyr Asn Lys Tyr Ser Pro Trp Leu
            915                 920                 925

Ser Leu Ile Pro Gly Val Asn Tyr Asp Leu Phe Glu Glu Leu Ala Val
            930                 935                 940

Arg Phe Gln Asn Ala Leu Gln Leu Tyr Asp Thr Arg Asn Leu Ile Gln
945                 950                 955                 960

Asn Gly Arg Phe Ile Asp Gly Leu Val Ser Trp Met Thr Thr Pro Gly
```

```
            965                 970                 975
Val Gln Val Arg Lys Asp Ser Ala Ser Ser Ile Leu Glu Leu Asn Ser
            980                 985                 990

Trp Glu Glu Gln Val Val Gln Lys Val Pro Val Cys Gln Gly Tyr Gly
            995                1000                1005

Tyr Val Leu Arg Val Thr Ala Ser Lys Glu Asp Leu Gly Glu Gly
        1010                1015                1020

Tyr Ile Lys Val Ser Asp Glu Met Gly Asn Ser Asp Thr Ile Ile
        1025                1030                1035

Phe Ser Ala Cys Asn Asn Ser Asn Asn Asp Val Ser Ile Asn Asn
        1040                1045                1050

Tyr Val Thr Gln Glu Leu Glu Phe Phe Pro Asp Ser Asp Tyr Val
        1055                1060                1065

His Leu Glu Ile Gly Glu Thr Glu Gly Thr Phe Gln Ile Val Ser
        1070                1075                1080

Val Glu Leu Ile Leu Met Glu Asp
        1085                1090

<210> SEQ ID NO 5
<211> LENGTH: 669
<212> TYPE: PRT
<213> ORGANISM: Bacillus thuringiensis

<400> SEQUENCE: 5

Met Lys Ile Asn Asp Val Asn Glu Trp Asp Asn Val Ala Glu Val Thr
1               5                   10                  15

Glu Asn Pro Leu Ala Pro Ser Ile Pro Tyr Asn Val Leu Gln Arg Lys
            20                  25                  30

Glu Asn Thr Ala Asn Glu Leu Thr Tyr Asp Asn Tyr Asn Phe Gln Asp
        35                  40                  45

Phe Leu Thr Leu Gly Tyr Glu Asp Ile Thr Gln Ala Ala Asn Ala Gln
    50                  55                  60

Asp Val Ile Asn Thr Thr Leu Asn Val Thr Ala Thr Ile Leu Asn Phe
65                  70                  75                  80

Leu Gly Val Pro Tyr Ala Gly Thr Val Ile Ser Met Tyr Gln Lys Leu
                85                  90                  95

Phe Asn Tyr Leu Trp Pro Tyr Glu Asp Thr Ser Glu Trp Asp Lys Met
            100                 105                 110

Met Ala Ala Val Glu Ala Leu Ile Asn Gln Lys Ile Asn Glu Thr Val
        115                 120                 125

Lys Ser Leu Ala Leu Ala Asp Leu Asp Gly Leu Gly Arg Asn Leu Lys
    130                 135                 140

Ser Tyr Gly Asn Ala Leu Lys Asn Trp Asn Glu Asn Lys Asn Asp Ala
145                 150                 155                 160

Asp Ser Thr Ala Leu Val Leu Asp Arg Phe Arg Thr Val Asn Glu Leu
                165                 170                 175

Phe Val Asn Asp Met Ala Ser Phe Ala Pro Lys Gly Tyr Glu Val Leu
            180                 185                 190

Leu Leu Asp Val Tyr Ala Lys Ala Ala Asn Leu His Leu Leu Phe Leu
        195                 200                 205

Arg Asp Ala Glu Leu Tyr Gly Ala Asp Trp Gly Met Pro Glu Asp Glu
    210                 215                 220

Ile Asn Leu Phe Tyr Gln Glu Gln Glu Asp Tyr Arg Lys Glu Tyr Ser
225                 230                 235                 240
```

-continued

```
Asp His Cys Ile Ser Trp Tyr Gln Lys Gly Leu Asn Gln Phe Asn Lys
            245                 250                 255
Ser Ser Ala Leu Asp Trp Ile Lys Tyr Asn Arg Tyr Arg Thr Gln Met
        260                 265                 270
Thr Ile Asn Val Leu Asp Phe Val Ala Leu Tyr Pro Asn Tyr Asp Val
    275                 280                 285
Arg Lys Tyr Pro Met Ser Thr His Thr Glu Leu Thr Arg Thr Val Tyr
290                 295                 300
Ser Asp Pro Ile Gly Phe Asp Glu Arg Thr Gly Thr Gly Thr Ser Gly
305                 310                 315                 320
Val Arg Ala Trp Tyr Glu Ala Gly Arg Ser Phe Ala Glu Ile Glu Asn
                325                 330                 335
Asn Ala Ile Pro Ala Pro Asp Ile Val Lys Phe Ile Asn Lys Leu Thr
            340                 345                 350
Val Tyr Ser Lys Arg Ile Asn Ala Ser Pro Phe Met Ala Thr Arg Trp
        355                 360                 365
Ala Gly His Ser Ile Thr Gln Asp Thr Thr Phe Thr Gly Ser Ala Gln
    370                 375                 380
Glu Ile Lys Tyr Gly Asp Val Ser Gly Val Pro Thr Thr Phe Leu Phe
385                 390                 395                 400
Lys Asn Thr Asp Ile Tyr Arg Thr Ile Ser Thr Val Gly Thr Tyr Tyr
                405                 410                 415
Tyr Thr Asn Gly Pro Tyr Lys Leu Pro Leu Ser Lys Val His Phe Tyr
            420                 425                 430
Gly Ile Asn Thr Ser Asn Arg Lys Glu Thr Phe Asn Tyr Asp Gln Asp
        435                 440                 445
Ile Asn Phe Lys Phe Gln His Gln Lys Asp Ser Ser Asn Glu Ile Ala
    450                 455                 460
Val Val Leu Pro Gly Pro Thr Asp Tyr Gly Asp Tyr Asn Lys Tyr Ser
465                 470                 475                 480
His Arg Leu Ser Tyr Ile Ser Asp Ala Pro Ile Lys Gln Phe Thr Gly
                485                 490                 495
Leu Ser Ser Asn Glu Gly Phe Val Pro Val Phe Gly Trp Met His Ser
            500                 505                 510
Ser Thr Thr Arg Lys Asn Phe Leu Ser Ala Asn Gln Ile Thr Gln Ile
        515                 520                 525
Pro Ala Val Lys Ser His Glu Tyr Asn Ser Ser Met Ala Ile Val Ser
    530                 535                 540
Ser Asn Gly Tyr Cys Gly Gly Tyr Ile Met Lys Val Ser Lys Val Phe
545                 550                 555                 560
Pro Phe Asn Glu Val Thr Ala Gly Asn Tyr Val Val Asp Cys Glu Asp
                565                 570                 575
Tyr Ser Gln Gln Phe Arg Phe Arg Val Arg Tyr Ala Ser Thr Val Ser
            580                 585                 590
Cys Pro Leu Arg Phe Ala Thr Phe Ser Ile Ser Gly Pro Thr Val Asn
        595                 600                 605
Leu Glu Lys Thr Leu Gln Lys Gly Asp Glu Ile Lys Tyr Ser Ser Phe
    610                 615                 620
Lys Tyr Ser Glu Tyr Ser Asp Pro Val Arg Phe Asn Pro Pro Gly Thr
625                 630                 635                 640
Ser Gly Phe Pro Ser Phe Asn Leu Ile Phe Val Gly Leu Ser Ala Asn
                645                 650                 655
Glu Asn Val Tyr Ile Asp Lys Ile Glu Cys Ile Pro Val
```

<210> SEQ ID NO 6
<211> LENGTH: 578
<212> TYPE: PRT
<213> ORGANISM: Bacillus thuringiensis

<400> SEQUENCE: 6

Met Tyr Gln Lys Leu Phe Asn Tyr Leu Trp Pro Tyr Glu Asp Thr Ser
1               5                   10                  15

Glu Trp Asp Lys Met Met Ala Ala Val Glu Ala Leu Ile Asn Gln Lys
            20                  25                  30

Ile Asn Glu Thr Val Lys Ser Leu Ala Leu Ala Asp Leu Asp Gly Leu
        35                  40                  45

Gly Arg Asn Leu Lys Ser Tyr Gly Asn Ala Leu Lys Asn Trp Asn Glu
    50                  55                  60

Asn Lys Asn Asp Ala Asp Ser Thr Ala Leu Val Leu Asp Arg Phe Arg
65                  70                  75                  80

Thr Val Asn Glu Leu Phe Val Asn Asp Met Ala Ser Phe Ala Pro Lys
                85                  90                  95

Gly Tyr Glu Val Leu Leu Leu Asp Val Tyr Ala Lys Ala Asn Leu
            100                 105                 110

His Leu Leu Phe Leu Arg Asp Ala Glu Leu Tyr Gly Ala Asp Trp Gly
        115                 120                 125

Met Pro Glu Asp Glu Ile Asn Leu Phe Tyr Gln Glu Gln Glu Asp Tyr
    130                 135                 140

Arg Lys Glu Tyr Ser Asp His Cys Ile Ser Trp Tyr Gln Lys Gly Leu
145                 150                 155                 160

Asn Gln Phe Asn Lys Ser Ser Ala Leu Asp Trp Ile Lys Tyr Asn Arg
                165                 170                 175

Tyr Arg Thr Gln Met Thr Ile Asn Val Leu Asp Phe Val Ala Leu Tyr
            180                 185                 190

Pro Asn Tyr Asp Val Arg Lys Tyr Pro Met Ser Thr His Thr Glu Leu
        195                 200                 205

Thr Arg Thr Val Tyr Ser Asp Pro Ile Gly Phe Asp Glu Arg Thr Gly
    210                 215                 220

Thr Gly Thr Ser Gly Val Arg Ala Trp Tyr Glu Ala Gly Arg Ser Phe
225                 230                 235                 240

Ala Glu Ile Glu Asn Asn Ala Ile Pro Ala Pro Asp Ile Val Lys Phe
                245                 250                 255

Ile Asn Lys Leu Thr Val Tyr Ser Lys Arg Ile Asn Ala Ser Pro Phe
            260                 265                 270

Met Ala Thr Arg Trp Ala Gly His Ser Ile Thr Gln Asp Thr Thr Phe
        275                 280                 285

Thr Gly Ser Ala Gln Glu Ile Lys Tyr Gly Asp Val Ser Gly Val Pro
    290                 295                 300

Thr Thr Phe Leu Phe Lys Asn Thr Asp Ile Tyr Arg Thr Ile Ser Thr
305                 310                 315                 320

Val Gly Thr Tyr Tyr Tyr Thr Asn Gly Pro Tyr Lys Leu Pro Leu Ser
                325                 330                 335

Lys Val His Phe Tyr Gly Ile Asn Thr Ser Asn Arg Lys Glu Thr Phe
            340                 345                 350

Asn Tyr Asp Gln Asp Ile Asn Phe Lys Phe Gln His Gln Lys Asp Ser
        355                 360                 365

```
Ser Asn Glu Ile Ala Val Val Leu Pro Gly Pro Thr Asp Tyr Gly Asp
    370             375             380

Tyr Asn Lys Tyr Ser His Arg Leu Ser Tyr Ile Ser Asp Ala Pro Ile
385             390             395             400

Lys Gln Phe Thr Gly Leu Ser Ser Asn Glu Gly Phe Val Pro Val Phe
            405             410             415

Gly Trp Met His Ser Ser Thr Thr Arg Lys Asn Phe Leu Ser Ala Asn
            420             425             430

Gln Ile Thr Gln Ile Pro Ala Val Lys Ser His Glu Tyr Asn Ser Ser
            435             440             445

Met Ala Ile Val Ser Ser Asn Gly Tyr Cys Gly Gly Tyr Ile Met Lys
450             455             460

Val Ser Lys Val Phe Pro Phe Asn Glu Val Thr Ala Gly Asn Tyr Val
465             470             475             480

Val Asp Cys Glu Asp Tyr Ser Gln Gln Phe Arg Phe Arg Val Arg Tyr
            485             490             495

Ala Ser Thr Val Ser Cys Pro Leu Arg Phe Ala Thr Phe Ser Ile Ser
            500             505             510

Gly Pro Thr Val Asn Leu Glu Lys Thr Leu Gln Lys Gly Asp Glu Ile
            515             520             525

Lys Tyr Ser Ser Phe Lys Tyr Ser Glu Tyr Ser Asp Pro Val Arg Phe
    530             535             540

Asn Pro Pro Gly Thr Ser Gly Phe Pro Ser Phe Asn Leu Ile Phe Val
545             550             555             560

Gly Leu Ser Ala Asn Glu Asn Val Tyr Ile Asp Lys Ile Glu Cys Ile
            565             570             575

Pro Val

<210> SEQ ID NO 7
<211> LENGTH: 4
<212> TYPE: PRT
<213> ORGANISM: Artificial sequence
<220> FEATURE:
<223> OTHER INFORMATION: endoplasmic reticulum targeting peptide

<400> SEQUENCE: 7

Lys Asp Glu Leu
1
```